(12) United States Patent
Patel et al.

(10) Patent No.: US 10,711,334 B2
(45) Date of Patent: Jul. 14, 2020

(54) METAL ALLOY FOR MEDICAL DEVICES

(71) Applicant: ICON MEDICAL CORP., Atlanta, GA (US)

(72) Inventors: Udayan Patel, San Jose, CA (US); Noah Roth, NE Atlanta, GA (US)

(73) Assignee: MIRUS LLC, Atlanta, GA (US)

( * ) Notice: Subject to any disclaimer, the term of this patent is extended or adjusted under 35 U.S.C. 154(b) by 235 days.

(21) Appl. No.: 15/027,766

(22) PCT Filed: Oct. 6, 2014

(86) PCT No.: PCT/US2014/059245
§ 371 (c)(1),
(2) Date: Apr. 7, 2016

(87) PCT Pub. No.: WO2015/054101
PCT Pub. Date: Apr. 16, 2015

(65) Prior Publication Data
US 2016/0237541 A1    Aug. 18, 2016

Related U.S. Application Data

(60) Provisional application No. 61/908,896, filed on Nov. 26, 2013, provisional application No. 61/895,072, (Continued)

(51) Int. Cl.
*C22F 1/18* (2006.01)
*C22C 27/04* (2006.01)
(Continued)

(52) U.S. Cl.
CPC ........... *C22F 1/18* (2013.01); *A61B 17/68* (2013.01); *A61C 5/77* (2017.02); *A61C 5/88* (2017.02);
(Continued)

(58) Field of Classification Search
CPC . A61B 17/68; A61B 2017/00526; A61C 5/77; A61C 5/88; A61C 7/00;
(Continued)

(56) References Cited

U.S. PATENT DOCUMENTS 5,437,744 A    8/1995 Carlen
5,674,242 A   10/1997 Phan et al.
(Continued)

FOREIGN PATENT DOCUMENTS

WO    2009070133    6/2009
WO    20090079282   6/2009

OTHER PUBLICATIONS

U.S. Searching Authority, International Search Report for related PCT/US2014/059245 (dated Jan. 21, 2015).
(Continued)

*Primary Examiner* — Jenny R Wu
(74) *Attorney, Agent, or Firm* — Fay Sharpe LLP

(57) ABSTRACT

A method and process for at least partially forming a medical device. The present invention is generally directed to a medical device that is at least partially made of a novel alloy having improved properties as compared to past medical devices. The novel alloy used to at least partially form the medical device improves one or more properties (e.g., strength, durability, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, improved fatigue life, crack resistance, crack propagation resistance, etc.) of such medical device.

14 Claims, 2 Drawing Sheets

Related U.S. Application Data filed on Oct. 24, 2013, provisional application No. 61/888,643, filed on Oct. 9, 2013.

(51) Int. Cl.

| | |
|---|---|
| *A61C 5/88* | (2017.01) |
| *A61C 5/77* | (2017.01) |
| *A61B 17/68* | (2006.01) |
| *A61C 7/00* | (2006.01) |
| *A61C 8/00* | (2006.01) |
| *B21B 3/00* | (2006.01) |
| *B21C 23/00* | (2006.01) |
| *B22D 21/00* | (2006.01) |
| *B22F 1/00* | (2006.01) |
| *B22F 3/04* | (2006.01) |
| *B22F 3/16* | (2006.01) |
| *B22F 5/00* | (2006.01) |
| *B23K 31/02* | (2006.01) |
| *C22C 27/02* | (2006.01) |
| *C23C 8/24* | (2006.01) |
| *C23C 8/80* | (2006.01) |
| *A61B 17/00* | (2006.01) |

(52) U.S. Cl.
CPC ............ *A61C 7/00* (2013.01); *A61C 8/0012* (2013.01); *B21B 3/00* (2013.01); *B21C 23/002* (2013.01); *B22D 21/005* (2013.01); *B22F 1/0003* (2013.01); *B22F 3/04* (2013.01); *B22F 3/16* (2013.01); *B22F 5/00* (2013.01); *B23K 31/02* (2013.01); *C22C 27/02* (2013.01); *C22C 27/04* (2013.01); *C23C 8/24* (2013.01); *C23C 8/80* (2013.01); *A61B 2017/00526* (2013.01); *B22F 2301/20* (2013.01)

(58) Field of Classification Search
CPC ....... A61C 8/0012; B21B 3/00; B21C 23/002; B22D 21/005; B22F 1/0003; B22F 2301/20; B22F 3/04; B22F 3/16; B22F 5/00; B23K 31/02; C22C 27/02; C22C 27/04; C22F 1/18; C23C 8/24; C23C 8/80
See application file for complete search history.

(56) References Cited

U.S. PATENT DOCUMENTS

| | | |
|---|---|---|
| 5,824,077 A | 10/1998 | Mayer |
| 2003/0003220 A1 | 1/2003 | Zhong et al. |
| 2004/0049261 A1 | 3/2004 | Xu |
| 2004/0236433 A1 | 11/2004 | Kennedy et al. |
| 2006/0198750 A1 | 9/2006 | Furst et al. |
| 2007/0077163 A1 | 4/2007 | Furst et al. |
| 2009/0005850 A1* | 1/2009 | Stinson ................ A61L 31/022 623/1.11 |
| 2011/0214785 A1 | 9/2011 | Buckman et al. |
| 2012/0316655 A1 | 12/2012 | Fuller et al. |
| 2013/0216421 A1 | 8/2013 | Buckman et al. |

OTHER PUBLICATIONS

European Patent Office, Supplementary European Search Report for corresponding application EP 14852817.7 (dated May 9, 2017).

* cited by examiner

METAL ALLOY FOR MEDICAL DEVICES

The present invention claims priority on U.S. Provisional Application Ser. No. 61/888,643 filed Oct. 9, 2013; 61/895,072 filed Oct. 24, 2013; and 61/908,896 filed Nov. 26, 2013, which are incorporated herein by reference.

The invention relates generally to medical devices, and particularly to a medical device that is at least partially formed of a novel alloy.

SUMMARY OF THE INVENTION

The present invention is generally directed to a medical device that is at least partially made of a novel alloy having improved properties as compared to past medical devices. The novel alloy used to at least partially form the medical device improves one or more properties (e.g., strength, durability, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, improved fatigue life, crack resistance, crack propagation resistance, etc.) of such medical device. These one or more improved physical properties of the novel alloy can be achieved in the medical device without having to increase the bulk, volume and/or weight of the medical device, and in some instances these improved physical properties can be obtained even when the volume, bulk and/or weight of the medical device is reduced as compared to medical devices that are at least partially formed from traditional stainless steel or cobalt and chromium alloy materials. However, it will be appreciated that the novel alloy can include metals such as stainless steel, cobalt and chromium, etc.

The novel alloy that is used to at least partially form the medical device can thus 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the longitudinal lengthening properties of the medical device, 10) improve the recoil properties of the medical device, 11) improve the friction coefficient of the medical device, 12) improve the heat sensitivity properties of the medical device, 13) improve the biostability and/or biocompatibility properties of the medical device, 14) increase fatigue resistance of the device, 15) resist cracking in the medical device and resist propagation of crack, and/or 16) enable smaller, thinner and/or lighter weight medical devices to be made. The medical device generally includes one or more materials that impart the desired properties to the medical device so as to withstand the manufacturing processes that are needed to produce the medical device. These manufacturing processes can include, but are not limited to, laser cutting, etching, crimping, annealing, drawing, pilgering, electroplating, electro-polishing, chemical polishing, cleaning, pickling, ion beam deposition or implantation, sputter coating, vacuum deposition, etc.

In another non-limiting aspect of the present invention, a medical device that can include the novel alloy is an orthopedic device, PFO (patent foramen ovale) device, stent, valve, spinal implant, vascular implant; graft, guide wire, sheath, stent catheter, electrophysiology catheter, hypotube, catheter, staple, cutting device, any type of implant, pacemaker, dental implant, bone implant, prosthetic implant or device to repair, replace and/or support a bone (e.g., acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, zygomatic bone, etc.) and/or cartilage, nail, rod, screw, post, cage, plate, pedicle screw, cap, hinge, joint system, wire, anchor, spacer, shaft, spinal implant, anchor, disk, ball, tension band, locking connector, or other structural assembly that is used in a body to support a structure, mount a structure and/or repair a structure in a body such as, but not limited to, a human body. In one non-limiting application, the medical device is a dental implant dental filling, dental tooth cap, dental bridge, braces for teeth, dental teeth cleaning equipment, and/or any other medical device used in the dental or orthodontist field. In another non-limiting application, the medical device is a stent. In still another non-limiting application, the medical device is a spinal implant. In yet another non-limiting application, the medical device is a prosthetic device. Although the present invention will be described with particular reference to medical devices, it will be appreciated that the novel alloy can be used in other components that are subjected to stresses that can lead to cracking and fatigue failure (e.g., automotive parts, springs, aerospace parts, industrial machinery, etc.).

In still another non-limiting aspect of the present invention, carbon nanotubes (CNT) can optionally be incorporated into a metal material to form the novel alloy. The metals that are used to form the novel alloy are non-limiting. The one or more metals used in the novel alloy generally have an alloy matrix and the CNT are incorporated within the grain structure of the alloy matrix; however, this is not required. It is believed that certain portions of the CNT will cross the grain boundary of the metal material and embed into the neighboring grains, thus forming an additional linkage between the grains. When a novel alloy is employed in dynamic application, a cyclic stress is applied on the alloy. At some point at a number of cycles, the novel alloy will crack due to fatigue failure that initiates and propagates along the grain boundaries. It is believed that the attachment of CNT across the grains will prevent or prolong crack propagation and fatigue failure. Further, when the grain size is large, the CNT gets completely embedded into a grain. The twinning of the grains is limited by the presence of CNT either fully embedded or partially embedded within the grain structure. Additionally, the CNT offers better surface erosion resistance. The novel alloy that includes the CNT can be made by powder metallurgy by adding the CNT to the metal powder or mixture of various metal powders to make a multi-component alloy. The mixture can then be compressed under high isostatic pressure into a preform where the particles of the powder fuse together and thereby trap the CNT into the matrix of the novel alloy. The preform can then be sintered under inert atmosphere or reducing atmosphere and at temperatures that will allow the metallic components to fuse and solidify. Depending on the desired grain structure, the fused metal can then be annealed or further processed into the final shape and then annealed. At no point should the novel alloy be heated above 300° C. without enclosing the novel alloy in an inert or reducing atmosphere and/or under vacuum. The material can also be processed in several other conventional ways. One in particular will be by metal injection molding or metal molding technique in which the metal and CNT are mixed with a binder to form a slurry. The slurry is then injected under pressure into a mold of desired shape. The slurry sets in the mold and is then removed. The binder is then sintered off in multiple steps leaving behind the densified metal-CNT composite. The novel alloy may be heated up to 1500° C. in an inert or reducing atmosphere and/or under vacuum. Most elemental metals and alloys have a fatigue life which limits its use in a dynamic application where cyclic load is applied during its use. The novel alloy prolongs the fatigue life of the medical device. The novel alloy is believed to have enhanced fatigue life, enhancing the bond strength between grain boundaries of the metal in the novel alloy, thus, inhibiting, preventing or prolonging the initiation and propagation of cracking that leads to fatigue failure. For example, in an orthopedic spinal application, the spinal rod implant undergoes repeated cycles throughout the patient's life and can potentially cause the spinal rod to crack. Titanium is commonly used in such devices; however, titanium has low fatigue resistance. The fatigue resistance can be improved by alloying the titanium metal with CNT in the manner described above. If higher strength as well as higher fatigue resistance is required, then the CNT can be alloyed with molybdenum-rhenium alloy to obtain such properties. With the addition of at least about 0.05 weight percent, typically at least about 0.5 wt %, and more typically about 0.5-5 wt % of CNT to the metal material of the novel alloy, the novel alloy can exhibit enhanced fatigue life.

In still another and/or alternative non-limiting aspect of the present invention, the metals that form the metal alloy of the present invention include, but are not limited to, iron, rhenium, molybdenum, calcium, chromium, cobalt, copper, gold, hafnium, iron, lead, magnesium, nickel, niobium, osmium, platinum, rare earth metals, silver, tantalum, technetium, titanium, tungsten, vanadium, yttrium, zinc, zirconium, and/or alloys of one or more of such metals (e.g., SS steel, MoRe alloy, CoCr alloy, TaW alloy, etc.). Although the novel alloy is described as including one or more metals, it can be appreciated that some or all of the metal in the novel alloy can be substituted for one or more materials selected form the group of ceramics, plastics, thermoplastics, thermosets, rubbers, laminates, non-wovens, etc.

In yet another and/or alternative non-limiting aspect of the present invention, the metals that form the metal alloy of the present invention include, but are not limited to, molybdenum and one or more alloying agents such as, but not limited to, calcium, carbon, cerium oxide, chromium, cobalt, copper, gold, hafnium, iron, lanthanum oxide, lead, magnesium, nickel, niobium, osmium, platinum, rare earth metals, rhenium, silver, tantalum, technetium, titanium, tungsten, vanadium, yttrium, yttrium oxide, zinc, zirconium, zirconium oxide, and/or alloys of one or more of such components (e.g., MoHfC, $MoY_2O_3$, $MoCe_2O$, MoW, MoTa, $MoZrO_2$, $MoLa_2O_3$, MoRe alloy, etc.). Although the novel alloy is described as including one or more metals and/or metal oxides, it can be appreciated that some or all of the metal and/or metal oxide in the novel alloy can be substituted for one or more materials selected from the group of ceramics, plastics, thermoplastics, thermosets, rubbers, laminates, non-wovens, etc.

In another and/or alternative non-limiting aspect of the present invention, the medical device is generally designed to include at least about 25 wt % of the novel metal alloy; however, this is not required. In one non-limiting embodiment of the invention, the medical device includes at least about 40 wt % of the novel metal alloy. In another and/or alternative non-limiting embodiment of the invention, the medical device includes at least about 50 wt % of the novel metal alloy. In still another and/or alternative non-limiting embodiment of the invention, the medical device includes at least about 60 wt % of the novel metal alloy. In yet another and/or alternative non-limiting embodiment of the invention, the medical device includes at least about 70 wt % of the novel metal alloy. In still yet another and/or alternative non-limiting embodiment of the invention, the medical device includes at least about 85 wt % of the novel metal alloy. In a further and/or alternative non-limiting embodiment of the invention, the medical device includes at least about 90 wt % of the novel metal alloy. In still a further and/or alternative non-limiting embodiment of the invention, the medical device includes at least about 95 wt % of the novel metal alloy. In yet a further and/or alternative non-limiting embodiment of the invention, the medical device includes about 100 wt % of the novel metal alloy.

In still another and/or alternative non-limiting aspect of the present invention, the novel metal alloy that is used to form all or part of the medical device 1) is not clad, metal sprayed, plated and/or formed (e.g., cold worked, hot worked, etc.) onto another metal, or 2) does not have another metal or metal alloy metal sprayed, plated, clad and/or formed onto the novel metal alloy. It will be appreciated that in some applications, the novel metal alloy of the present invention may be clad, metal sprayed, plated and/or formed onto another metal, or another metal or metal alloy may be plated, metal sprayed, clad and/or formed onto the novel metal alloy, when forming all or a portion of a medical device.

In yet another and/or alternative non-limiting aspect of the present invention, the novel alloy can be used to form a coating on a portion of all of a medical device. For example, the novel alloy can be used as a coating on articulation points of artificial joints. Such a coating can provide the benefit of better wear, scratch resistance, and/or elimination of leaching harmful metallic ions (i.e., Co, Cr, etc.) from the articulating surfaces when they undergo fretting (i.e., scratching during relative motion). As can be appreciated, the novel alloy can have other or additional advantages. As can also be appreciated, the novel alloy can be coated on other or additional types of medical devices. The coating thickness of the novel alloy is non-limiting. In one non-limiting example, there is provided a medical device in the form of a clad rod wherein the core of the rod is formed of a metal or novel alloy (e.g., iron, CoCr alloy, titanium alloy, SS steel, MoHfC, $MoY_2O_3$, $MoCe_2O$, MoW, MoTa, $MoZrO_2$, MoRe alloy, etc.) or ceramic or composite material, and the other layer of the clad rod is formed of the novel alloy. The core and the other layer of the rod can each form 50-99% of the overall cross section of the rod. As can also be appreciated, the novel alloy can form the outer layer of other or additional types of medical devices. The coating can be used to create a hard surface on the medical device at specific locations as well as all over the surface. The base hardness of novel alloy can be as low as 300 Vickers and/or as high as 500 Vickers. However, at high hardness these properties may not be desirable. In instances where the properties of fully annealed material are desired, but only the surface requires to be hardened as in this invention, the present invention includes a method that can provide benefits of both a softer metal alloy with a harder outer surface or shell. A non-limiting example is an orthopedic screw where a softer iron alloy is desired for high ductility as well as ease of machinability. Simultaneously, a hard shell is desired of the finished screw. While the inner hardness can range from 250 Vickers to 550 Vickers, the outer hardess can vary from 350 Vickers to 1000 Vickers when using novel alloy (e.g., MoHfC, MoY$_2$O$_3$, MoCe$_2$O, MoW, MoTa, MoZrO$_2$, MoRe alloy, Co—Cr alloy, Ta—W alloy, etc.).

In still yet another and/or alternative non-limiting aspect of the present invention, the novel alloy can be used to form a core of a portion or all of a medical device. For example, a medical device can be in the form of a rod. The core of the rod can be formed of the novel alloy and then the outside of the core can then be coated with one or more other materials (e.g., another type of metal or novel alloy, polymer coating, ceramic coating, composite material coating, etc.). Such a rod can be used, for example, for orthopedic applications such as, but not limited to, spinal rods and/or pedicle screw systems. Non-limiting benefits of using the novel alloy in the core of a medical device can include reducing the size of the medical device, increasing the strength of the medical device, and/or maintaining or reducing the cost of the medical device. As can be appreciated, the novel alloy can have other or additional advantages. As can also be appreciated, the novel alloy can form the core of other or additional types of medical devices. The core size and/or thickness of the novel alloy are non-limiting. In one non-limiting example, there is provided a medical device in the form of a clad rod wherein the core of the rod is formed of a novel alloy, and the other layer of the clad rod is formed of a metal or novel alloy (e.g., CoCr alloy, titanium alloy, SS steel, MoHfC, MoY$_2$O$_3$, MoCe$_2$O, MoW, MoTa, MoZrO$_2$, MoRe alloy, Ta—W alloy, etc.). The core and the other layer of the rod can each form 50-99% of the overall cross section of the rod. As can also be appreciated, the novel alloy can form the core of other or additional types of medical devices.

In another and/or alternative non-limiting aspect of the present invention, the novel alloy is used to form all or a portion of the medical device. In particular, a novel alloy includes rhenium and molybdenum. The novel alloy can include one or more other metals such as, but not limited to, calcium, chromium, cobalt, copper, gold, hafnium, iron, lead, magnesium, nickel, niobium, osmium, platinum, rare earth metals, silver, tantalum, technetium, titanium, tungsten, vanadium, yttrium, zinc, zirconium, and/or alloys thereof. In one non-limiting formulation, the novel alloy includes at least about 20 wt % rhenium, at least 20 wt % molybdenum, the total content of the rhenium and molybdenum in the novel alloy is at least 50 wt %, and the novel alloy can optionally include one or more metals selected from the group of hafnium, niobium, osmium, platinum, technetium, titanium, tungsten, vanadium, and zirconium. In this non-limiting formulation, the total content of the one or more optional metals is generally up to 45 wt %.

In another and/or alternative non-limiting aspect of the present invention, the novel alloy is used to form all or a portion of the medical device. In particular, a novel alloy includes molybdenum and one or more alloying agents such as, but not limited to, calcium, carbon, cerium oxide, chromium, cobalt, copper, gold, hafnium, iron, lanthanum oxide, lead, magnesium, nickel, niobium, osmium, platinum, rare earth metals, rhenium, silver, tantalum, technetium, titanium, tungsten, vanadium, yttrium, yttrium oxide, zinc, zirconium, zirconium oxide, and/or alloys of one or more of such components (e.g., MoHfC, MoY$_2$O$_3$, MoCe$_2$O, MoW, MoTa, MoZrO$_2$, MoLa$_2$O$_3$, MoRe alloy, etc.). In one non-limiting formulation, the novel alloy includes 40 wt % to 99.9 wt % molybdenum (e.g., 40 wt %, 40.01 wt %, 40.02 wt % 99.88 wt %, 99.89 wt %, 99.9 wt %) and any value or range therebetween.

In still another and/or alternative non-limiting aspect of the present invention, the novel alloy that is used to form all or a portion of the medical device is a novel alloy that includes 40 wt % to 99.9 wt % molybdenum (e.g., 40 wt %, 40.01 wt %, 40.02 wt % 99.88 wt %, 99.89 wt %, 99.9 wt %) and any value or range therebetween and optionally 0.01 weight percent to 5 weight percent CNT (e.g., 0.01 wt %, 0.011 wt %, 0.012 wt % 4.998 wt %, 4.999 wt %, 5 wt %) and any value or range therebetween.

In still yet another and/or alternative non-limiting aspect of the present invention, the novel alloy that is used to form all or a portion of the medical device is a novel alloy that includes molybdenum and one or more alloying agents such as, but not limited to, calcium, carbon, cerium oxide, chromium, cobalt, copper, gold, hafnium, iron, lanthanum oxide, lead, magnesium, nickel, niobium, osmium, platinum, rare earth metals, rhenium, silver, tantalum, technetium, titanium, tungsten, vanadium, yttrium, yttrium oxide, zinc, zirconium, zirconium oxide, and/or alloys of one or more of such components (e.g., MoHfC, MoY$_2$O$_3$, MoCe$_2$O, MoW, MoTa, MoZrO$_2$, MoLa$_2$O$_3$, MoRe alloy, etc.). The addition of controlled amounts of the alloying agents to the molybdenum alloy has been found to form a novel alloy that has improved physical properties. For instance, the addition of controlled amounts of carbon, cerium oxide, hafnium, lanthanum oxide, rhenium, tantalum, tungsten, yttrium oxide, zirconium oxide to the molybdenum alloy can result in 1) an increase in yield strength of the alloy, 2) an increase in tensile elongation of the alloy, 3) an increase in ductility of the alloy, 4) a reduction in grain size of the alloy, 5) a reduction in the amount of free carbon, oxygen and/or nitrogen in the alloy, and/or 6) a reduction in the tendency of the alloy to form micro-cracks during the forming of the alloy into a medical device.

In still another and/or alternative non-limiting aspect of the present invention, the novel alloy that is used to form all or a portion of the medical device is a novel alloy that includes at least about 90 wt % molybdenum and rhenium and optionally up to about 5 wt % CNT. In one non-limiting composition, the content of molybdenum and rhenium in the novel alloy is at least about 95 wt %. In another and/or alternative non-limiting composition, the content of molybdenum and rhenium in the novel alloy is at least about 97 wt %. In still another and/or alternative non-limiting composition, the content of molybdenum and rhenium in the novel alloy is at least about 98 wt %. In yet another and/or alternative non-limiting composition, the content of molybdenum and rhenium in the novel alloy is at least about 99 wt %. In still yet another and/or alternative non-limiting composition, the content of molybdenum and rhenium in the novel alloy is at least about 99.5 wt %. As can be appreciated, other weight percentages of the rhenium and molybdenum content of the novel alloy can be used.

In one non-limiting composition, the purity level of the novel alloy is such so as to produce a solid solution of the novel alloy. A solid solution or homogeneous solution is defined as a novel alloy that includes two or more primary metals and the combined weight percent of the primary metals is at least about 95 wt %. A primary metal is a metal component of the novel alloy that is not a metal impurity. A solid solution of a novel alloy that includes rhenium and molybdenum as the primary metals is an alloy that includes at least about 95 wt % rhenium and molybdenum. In one non-limiting composition, the rhenium content of the novel alloy is at least about 10 wt %. In another non-limiting composition, the rhenium content of the novel alloy is at least about 30 wt %. In yet another non-limiting composition, the rhenium content of the novel alloy is at least about 40 wt %. In another and/or alternative non-limiting composition, the rhenium content of the novel alloy is about 45 wt %. In still another and/or alternative non-limiting composition, the rhenium content of the novel alloy is about 45-50 wt %. In yet another and/or alternative non-limiting composition, the rhenium content of the novel alloy is about 47-48 wt %. In still yet another and/or alternative non-limiting composition, the rhenium content of the novel alloy is about 47.6-49.5 wt %. In still yet another and/or alternative non-limiting composition, the rhenium content of the novel alloy is about 10-60 wt %. As can be appreciated, other weight percentages of the rhenium content of the novel alloy can be used. In another and/or alternative embodiment of the invention, the molybdenum content of the novel alloy in accordance with the present invention is at least about 35 wt %. In one non-limiting composition, the molybdenum content of the novel alloy is at least about 20 wt %. In another non-limiting composition, the molybdenum content of the novel alloy is at least about 40 wt %. In yet another non-limiting composition, the molybdenum content of the novel alloy is at least about 45 wt %. In still another and/or alternative non-limiting composition, the molybdenum content of the novel alloy is at least about 50 wt %. In yet another and/or alternative non-limiting composition, the molybdenum content of the novel alloy is about 50-60 percent. In still yet another and/or alternative non-limiting composition, the molybdenum content of the novel alloy is about 50-56 wt %. In still yet another and/or alternative non-limiting composition, the molybdenum content of the novel alloy is about 40-90 wt %. In another and/or alternative non-limiting composition, the molybdenum content of the novel alloy is about 35-90 wt %, and the rhenium content of the novel alloy is about 35-90 wt %. In still another and/or alternative non-limiting composition, the molybdenum content of the novel alloy is about 35-90 wt %, and the rhenium content of the novel alloy is about 35-90 weight percent and the combined rhenium content and molybdenum content of the novel alloy is about 50-99.95 wt %. As can be appreciated, other weight percentages of the molybdenum content of the novel alloy can be used.

In still yet another and/or alternative non-limiting aspect of the present invention, the novel alloy that is used to form all or a portion of the medical device is a novel alloy that includes at least about 90 wt % molybdenum and rhenium, and optionally at least one additional metal which includes hafnium, niobium, osmium, platinum, technetium, titanium, tungsten, vanadium, and/or zirconium. The addition of controlled amounts of hafnium, niobium, osmium, platinum, technetium, titanium, tungsten, vanadium, and/or zirconium to the molybdenum and rhenium alloy has been found to form a novel alloy that has improved physical properties over a novel alloy that principally includes molybdenum and rhenium. For instance, the addition of controlled amounts of hafnium, niobium, osmium, platinum, technetium, titanium, tungsten, vanadium, and/or zirconium to the molybdenum and rhenium alloy can result in 1) an increase in yield strength of the alloy as compared to a novel alloy that principally includes molybdenum and rhenium, 2) an increase in tensile elongation of the alloy as compared to a novel alloy that principally includes molybdenum and rhenium, 3) an increase in ductility of the alloy as compared to a novel alloy that principally includes molybdenum and rhenium, 4) a reduction in grain size of the alloy as compared to a novel alloy that principally includes molybdenum and rhenium, 5) a reduction in the amount of free carbon, oxygen and/or nitrogen in the alloy as compared to a novel alloy that principally includes molybdenum and rhenium, and/or 6) a reduction in the tendency of the alloy to form micro-cracks during the forming of the alloy into a medical device as compared to the forming of a medical device from a novel alloy that principally includes molybdenum and rhenium. In one non-limiting composition, the content of molybdenum and rhenium and the at least one additional metal in the novel alloy is at least about 90 wt %. In another and/or alternative non-limiting composition, the content of molybdenum and rhenium and the at least one additional metal in the novel alloy is at least about 95 wt %. In still another and/or alternative non-limiting composition, the content of molybdenum and rhenium and the at least one additional metal in the novel alloy is at least about 98 wt %. In yet another and/or alternative non-limiting composition, the content of molybdenum and rhenium and the at least one additional metal in the novel alloy is at least about 99 wt %. In still yet another and/or alternative non-limiting composition, the content of molybdenum and rhenium and the at least one additional metal in the novel alloy is at least about 99.5 wt %. In a further one non-limiting composition, the content of molybdenum and rhenium and the at least one additional metal in the novel alloy is at least about 99.9 wt %. In still a further and/or alternative non-limiting composition, the content of molybdenum and rhenium and the at least one additional metal in the novel alloy is at least about 99.95 wt %. As can be appreciated, other weight percentages of the content of molybdenum and rhenium and the at least one additional metal in the novel alloy can be used.

In one non-limiting composition, the purity level of the novel alloy is such so as to produce a solid solution of a rhenium and molybdenum and the at least one additional metal. A solid solution of a novel alloy that includes rhenium and molybdenum and the at least one additional metal of titanium, yttrium and/or zirconium as the primary metals is an alloy that includes at least about 95-99 wt % rhenium and molybdenum and the at least one additional metal. It is believed that a purity level of less than 95 wt % molybdenum and rhenium and the at least one additional metal adversely affects one or more physical properties of the novel alloy that are useful or desired in forming and/or using a medical device. In one embodiment of the invention, the rhenium content of the novel alloy in accordance with the present invention is at least about 40 wt %. In one non-limiting composition, the rhenium content of the novel alloy is at least about 45 wt %. In still another and/or alternative non-limiting composition, the rhenium content of the novel alloy is about 45-50 wt %. In yet another and/or alternative non-limiting composition, the rhenium content of the novel alloy is about 47-48 wt %. As can be appreciated, other weight percentages of the rhenium content of the novel alloy can be used. In another and/or alternative embodiment of the invention, the molybdenum content of the novel alloy is at least about 40 wt %. In one non-limiting composition, the molybdenum content of the novel alloy is at least about 45 wt %. In another and/or alternative non-limiting composition, the molybdenum content of the novel alloy is at least about 50 wt %. In still another and/or alternative non-limiting composition, the molybdenum content of the novel alloy is about 50-60 percent. In yet another and/or alternative non-limiting composition, the molybdenum content of the novel alloy is about 50-56 wt %. As can be appreciated, other weight percentages of the molybdenum content of the novel alloy can be used. The combined content of hafnium, niobium, osmium, platinum, technetium, titanium, tungsten, vanadium, and/or zirconium in the novel alloy is generally less than 45 wt %, typically less than about 25 wt %, more typically less than about 10 wt %, still more typically less than about 5 wt %, yet more typically no more than about 1 wt %, and still yet more typically no more than about 0.5 wt %.

In still another and/or alternative non-limiting aspect of the present invention, the novel metal alloy that is used to form all or a portion of the medical device is a novel metal alloy that includes at least about 90 wt % molybdenum and rhenium. In one non-limiting composition, the content of molybdenum and rhenium in the novel metal alloy is at least about 95 wt %. In another and/or alternative non-limiting composition, the content of molybdenum and rhenium in the novel metal alloy is at least about 97 wt %. In still another and/or alternative non-limiting composition, the content of molybdenum and rhenium in the novel metal alloy is at least about 98 wt %. In yet another and/or alternative non-limiting composition, the content of molybdenum and rhenium in the novel metal alloy is at least about 99 wt %. In still yet another and/or alternative non-limiting composition, the content of molybdenum and rhenium in the novel metal alloy is at least about 99.5 wt %. In a further one non-limiting composition, the content of molybdenum and rhenium in the novel metal alloy is at least about 99.9 wt %. In still a further and/or alternative non-limiting composition, the content of molybdenum and rhenium in the novel metal alloy is at least about 99.95 wt %. In yet a further and/or alternative non-limiting composition, the content of molybdenum and rhenium in the novel metal alloy is at least about 99.99 wt %. As can be appreciated, other weight percentages of the rhenium and molybdenum content of the novel metal alloy can be used.

In one non-limiting composition, the purity level of the novel metal alloy is such so as to produce a solid solution of the novel metal alloy. A solid solution or homogeneous solution is defined as a metal alloy that includes two or more primary metals and the combined weight percent of the primary metals is at least about 95 w %, typically at least about 99 wt %, more typically at least about 99.5 wt %, even more typically at least about 99.8 wt %, and still even more typically at least about 99.9 wt %. A primary metal is a metal component of the metal alloy that is not a metal impurity. A solid solution of a novel metal alloy that includes rhenium and molybdenum as the primary metals is an alloy that includes at least about 95-99 wt % rhenium and molybdenum. It is believed that a purity level of less than 95 wt % molybdenum and rhenium adversely affects one or more physical properties of the metal alloy that are useful or desired in forming and/or using a medical device.

In one embodiment of the invention, the rhenium content of the novel metal alloy in accordance with the present invention is at last about 35 wt %. In one non-limiting composition, the rhenium content of the novel metal alloy is at least about 40 wt %. In another and/or alternative non-limiting composition, the rhenium content of the novel metal alloy is about 45 wt %. In still another and/or alternative non-limiting composition, the rhenium content of the novel metal alloy is about 45-50 wt %. In yet another and/or alternative non-limiting composition, the rhenium content of the novel metal alloy is about 47-48 wt %. In still yet another and/or alternative non-limiting composition, the rhenium content of the novel metal alloy is about 47.6-49.5 wt %. As can be appreciated, other weight percentages of the rhenium content of the novel metal alloy can be used. In another and/or alternative embodiment of the invention, the molybdenum content of the novel metal alloy in accordance with the present invention is at least about 35 wt %. In one non-limiting composition, the molybdenum content of the novel metal alloy is at least about 40 wt %. In another non-limiting composition, the molybdenum content of the novel metal alloy is at least about 45 wt %. In still another and/or alternative non-limiting composition, the molybdenum content of the novel metal alloy is at least about 50 wt %. In yet another and/or alternative non-limiting composition, the molybdenum content of the novel metal alloy is about 50-60 percent. In still yet another and/or alternative non-limiting composition, the molybdenum content of the novel metal alloy is about 50-56 wt %. In another and/or alternative non-limiting composition, the molybdenum content of the novel metal alloy is about 35-90 wt %, and the rhenium content of the novel metal alloy is about 35-90 wt %. In still another and/or alternative non-limiting composition, the molybdenum content of the novel metal alloy is about 35-90 wt %, and the rhenium content of the novel metal alloy is about 35-90 wt % and the combined rhenium content and molybdenum content of the novel metal alloy is about 50-100 wt %. As can be appreciated, other weight percentages of the molybdenum content of the novel metal alloy can be used.

In still yet another and/or alternative non-limiting aspect of the present invention, the novel metal alloy that is used to form all or a portion of the medical device is a novel metal alloy that includes at least about 90 wt % molybdenum and rhenium, and at least one additional metal which includes titanium, yttrium, and/or zirconium. The addition of controlled amounts of titanium, yttrium, and/or zirconium to the molybdenum and rhenium alloy has been found to form a metal alloy that has improved physical properties over a metal alloy that principally includes molybdenum and rhenium. For instance, the addition of controlled amounts of titanium, yttrium, and/or zirconium to the molybdenum and rhenium alloy can result in 1) an increase in yield strength of the alloy as compared to a metal alloy that principally includes molybdenum and rhenium, 2) an increase in tensile elongation of the alloy as compared to a metal alloy that principally includes molybdenum and rhenium, 3) an increase in ductility of the alloy as compared to a metal alloy that principally includes molybdenum and rhenium, 4) a reduction in grain size of the alloy as compared to a metal alloy that principally includes molybdenum and rhenium, 5) a reduction in the amount of free carbon, oxygen and/or nitrogen in the alloy as compared to a metal alloy that principally includes molybdenum and rhenium, and/or 6) a reduction in the tendency of the alloy to form micro-cracks during the forming of the alloy into a medical device as compared to the forming of a medical device from a metal alloy that principally includes molybdenum and rhenium. In one non-limiting composition, the content of molybdenum and rhenium and the at least one additional metal in the novel metal alloy is at least about 90 wt %. In another and/or alternative non-limiting composition, the content of molybdenum and rhenium and the at least one additional metal in the novel metal alloy is at least about 95 wt %. In still another and/or alternative non-limiting composition, the content of molybdenum and rhenium and the at least one additional metal in the novel metal alloy is at least about 98 wt %. In yet another and/or alternative non-limiting composition, the content of molybdenum and rhenium and the at least one additional metal in the novel metal alloy is at least about 99 wt %. In still yet another and/or alternative non-limiting composition, the content of molybdenum and rhenium and the at least one additional metal in the novel metal alloy is at least about 99.5 wt %. In a further one non-limiting composition, the content of molybdenum and rhenium and the at least one additional metal in the novel metal alloy is at least about 99.9 wt %. In still a further and/or alternative non-limiting composition, the content of molybdenum and rhenium and the at least one additional metal in the novel metal alloy is at least about 99.95 wt %. In yet a further and/or alternative non-limiting composition, the content of molybdenum and rhenium and the at least one additional metal in the novel metal alloy is at least about 99.99 wt %. As can be appreciated, other weight percentages of the content of molybdenum and rhenium and the at least one additional metal in the novel metal alloy can be used.

In one non-limiting composition, the purity level of the novel metal alloy is such so as to produce a solid solution of rhenium and molybdenum and the at least one additional metal. A solid solution of a novel metal alloy that includes rhenium and molybdenum and the at least one additional metal of titanium, yttrium and/or zirconium as the primary metals is an alloy that includes at least about 95-99 wt % rhenium and molybdenum and the at least one additional metal. It is believed that a purity level of less than 95 wt % molybdenum and rhenium and the at least one additional metal adversely affects one or more physical properties of the metal alloy that are useful or desired in forming and/or using a medical device. In one embodiment of the invention, the rhenium content of the novel metal alloy in accordance with the present invention is at least about 40 wt %. In one non-limiting composition, the rhenium content of the novel metal alloy is at least about 45 wt %. In still another and/or alternative non-limiting composition, the rhenium content of the novel metal alloy is about 45-50 wt %. In yet another and/or alternative non-limiting composition, the rhenium content of the novel metal alloy is about 47-48 wt %. As can be appreciated, other weight percentages of the rhenium content of the novel metal alloy can be used. In another and/or alternative embodiment of the invention, the molybdenum content of the novel metal alloy is at least about 40 wt %. In one non-limiting composition, the molybdenum content of the novel metal alloy is at least about 45 wt %. In another and/or alternative non-limiting composition, the molybdenum content of the novel metal alloy is at least about 50 wt %. In still another and/or alternative non-limiting composition, the molybdenum content of the novel metal alloy is about 50-60 percent. In yet another and/or alternative non-limiting composition, the molybdenum content of the novel metal alloy is about 50-56 wt %. As can be appreciated, other weight percentages of the molybdenum content of the novel metal alloy can be used.

The combined content of titanium, yttrium and zirconium in the novel metal alloy is less than about 5 wt %, typically no more than about 1 wt %, and more typically no more than about 0.5 wt %. A higher weight percent content of titanium, yttrium and/or zirconium in the novel metal alloy can begin to adversely affect the brittleness of the novel metal alloy. When titanium is included in the novel metal alloy, the titanium content is typically less than about 1 wt %, more typically less than about 0.6 wt %, even more typically about 0.05-0.5 wt %, still even more typically about 0.1-0.5 wt %. As can be appreciated, other weight percentages of the titanium content of the novel metal alloy can be used. When zirconium is included in the novel metal alloy, the zirconium content is typically less than about 0.5 wt %, more typically less than about 0.3 wt %, even more typically about 0.01-0.25 wt %, still even more typically about 0.05-0.25 wt %. As can be appreciated, other weight percentages of the zirconium content of the novel metal alloy can be used. When titanium and zirconium are included in the novel metal alloy, the weight ratio of titanium to zirconium is about 1-10:1, typically about 1.5-5:1, and more typically about 1.75-2.5:1. When yttrium is included in the novel metal alloy, the yttrium content is typically less than about 0.3 wt %, more typically less than about 0.2 wt %, and even more typically about 0.01-0.1 wt %. As can be appreciated, other weight percentages of the yttrium content of the novel metal alloy can be used. The inclusion of titanium, yttrium and/or zirconium in the novel metal alloy is believed to result in a reduction of oxygen trapped in the solid solution of the novel metal alloy. The reduction of trapped oxygen enables the formation of a smaller grain size in the novel metal alloy and/or an increase in the ductility of the novel metal alloy. The reduction of trapped oxygen in the novel metal alloy can also increase the yield strength of the novel metal alloy as compared to alloys of only molybdenum and rhenium (i.e., 2-10% increase). The inclusion of titanium, yttrium and/or zirconium in the novel metal alloy is also believed to cause a reduction in the trapped free carbon in the novel metal alloy. The inclusion of titanium, yttrium and/or zirconium in the novel metal alloy is believed to form carbides with the free carbon in the novel metal alloy. This carbide formation is also believed to improve the ductility of the novel metal alloy and to also reduce the incidence of cracking during the forming of the metal alloy into a medical device (e.g., medical device, etc.). As such, the novel metal alloy exhibits increased tensile elongation as compared to alloys of only molybdenum and rhenium (i.e., 1-8% increase). The inclusion of titanium, yttrium and/or zirconium in the novel metal alloy is also believed to cause a reduction in the trapped free nitrogen in the novel metal alloy. The inclusion of titanium, yttrium and/or zirconium in the novel metal alloy is believed to form carbo-nitrides with the free carbon and free nitrogen in the novel metal alloy. This carbo-nitride formation is also believed to improve the ductility of the novel metal alloy and to also reduce the incidence of cracking during the forming of the metal alloy into a medical device (e.g., medical device, etc.). As such, the novel metal alloy exhibits increased tensile elongation as compared to alloys of only molybdenum and rhenium (i.e., 1-8% increase). The reduction in the amount of free carbon, oxygen and/or nitrogen in the novel metal alloy is also believed to increase the density of the novel metal alloy (i.e., 1-5% increase). The formation of carbides, carbo-nitrides, and/or oxides in the novel metal alloy results in the formation of dispersed second phase particles in the novel metal alloy, thereby facilitating in the formation of small grain sizes in the metal alloy.

In still another and/or alternative non-limiting aspect of the present invention, the novel alloy includes less than about 5 wt % other metals and/or impurities. A high purity level of the novel alloy results in the formation of a more homogeneous alloy, which in turn results in a more uniform density throughout the novel alloy and also results in the desired yield and ultimate tensile strengths of the novel alloy. The density of the novel alloy is generally at least about 12 gm/cc, and typically at least about 13-13.5 gm/cc. This substantially uniform high density of the novel alloy significantly improves the radiopacity of the novel alloy. In one non-limiting composition, the novel alloy includes less than about 1 wt % other metals and/or impurities. In another and/or alternative non-limiting composition, the novel alloy includes less than about 0.5 wt % other metals and/or impurities. In still another and/or alternative non-limiting composition, the novel alloy includes less than about 0.4 wt % other metals and/or impurities. In yet another and/or alternative non-limiting composition, the novel alloy includes less than about 0.2 wt % other metals and/or impurities. In still yet another and/or alternative non-limiting composition, the novel alloy includes less than about 0.1 wt % other metals and/or impurities. In a further and/or alternative non-limiting composition, the novel alloy includes less than about 0.05 wt % other metals and/or impurities. In still a further and/or alternative non-limiting composition, the novel alloy includes less than about 0.02 wt % other metals and/or impurities. In yet a further and/or alternative non-limiting composition, the novel alloy includes less than about 0.01 wt % other metals and/or impurities. As can be appreciated, other weight percentages of the amount of other metals and/or impurities in the novel alloy can exist.

In yet another and/or alternative non-limiting aspect of the present invention, the novel alloy includes a certain amount of carbon and oxygen; however, this is not required. These two elements have been found to affect the forming properties and brittleness of the novel alloy. The controlled atomic ratio of carbon and oxygen of the novel alloy also can be used to minimize the tendency of the novel alloy to form micro-cracks during the forming of the novel alloy into a medical device, and/or during the use and/or expansion of the medical device in a body passageway. The control of the atomic ratio of carbon to oxygen in the novel alloy allows for the redistribution of oxygen in the novel alloy so as to minimize the tendency of micro-cracking in the novel alloy during the forming of the novel alloy into a medical device, and/or during the use and/or expansion of the medical device in a body passageway. The atomic ratio of carbon to oxygen in the novel alloy is believed to minimize the tendency of micro-cracking in the novel alloy, improve the degree of elongation of the novel alloy, both of which can affect one or more physical properties of the novel alloy that are useful or desired in forming and/or using the medical device. The carbon to oxygen atomic ratio can be as low as about 0.2:1. In one non-limiting formulation, the carbon to oxygen atomic ratio in the novel alloy is generally at least about 0.4:1 (i.e., weight ratio of about 0.3:1). In another non-limiting formulation, the carbon to oxygen atomic ratio in the novel alloy is generally at least about 0.5:1 (i.e., weight ratio of about 0.375:1). In still another non-limiting formulation, the carbon to oxygen atomic ratio in the novel alloy is generally at least about 1:1 (i.e., weight ratio of about 0.75:1). In yet another non-limiting formulation, the carbon to oxygen atomic ratio in the novel alloy is generally at least about 2:1 (i.e., weight ratio of about 1.5:1). In still yet another non-limiting formulation, the carbon to oxygen atomic ratio in the novel alloy is generally at least about 2.5:1 (i.e., weight ratio of about 1.88:1). In still another non-limiting formulation, the carbon to oxygen atomic ratio in the novel alloy is generally at least about 3:1 (i.e., weight ratio of about 2.25:1). In yet another non-limiting formulation, the carbon to oxygen atomic ratio of the novel alloy is generally at least about 4:1 (i.e., weight ratio of about 3:1). In still yet another non-limiting formulation, the carbon to oxygen atomic ratio of the novel alloy is generally at least about 5:1 (i.e., weight ratio of about 3.75:1). In still another non-limiting formulation, the carbon to oxygen atomic ratio in the novel alloy is generally about 2.5-50:1 (i.e., weight ratio of about 1.88-37.54:1). In a further non-limiting formulation, the carbon to oxygen atomic ratio in the novel alloy is generally about 2.5-20:1 (i.e., weight ratio of about 1.88-15:1). In a further non-limiting formulation, the carbon to oxygen atomic ratio in the novel alloy is generally about 2.5-13.3:1 (i.e., weight ratio of about 1.88-10:1). In still a further non-limiting formulation, the carbon to oxygen atomic ratio in the novel alloy is generally about 2.5-10:1 (i.e., weight ratio of about 1.88-7.5:1). In yet a further non-limiting formulation, the carbon to oxygen atomic ratio in the novel alloy is generally about 2.5-5:1 (i.e., weight ratio of about 1.88-3.75:1). As can be appreciated, other atomic ratios of the carbon to oxygen in the novel alloy can be used.

The carbon to oxygen ratio can be adjusted by intentionally adding carbon to the novel alloy until the desired carbon to oxygen ratio is obtained. Typically, the carbon content of the novel alloy is less than about 0.2 wt %. Carbon contents that are too large can adversely affect the physical properties of the novel alloy. In one non-limiting formulation, the carbon content of the novel alloy is less than about 0.1 wt % of the novel alloy. In another non-limiting formulation, the carbon content of the novel alloy is less than about 0.05 wt % of the novel alloy of the novel alloy. In still another non-limiting formulation, the carbon content of the novel alloy is less than about 0.04 wt % of the novel alloy. When carbon is not intentionally added to the novel alloy of the novel alloy, the novel alloy can include up to about 150 ppm carbon, typically up to about 100 ppm carbon, and more typically less than about 50 ppm carbon. The oxygen content of the novel alloy can vary depending on the processing parameters used to form the novel alloy of the novel alloy. Generally, the oxygen content is to be maintained at very low levels. In one non-limiting formulation, the oxygen content is less than about 0.1 wt % of the novel alloy. In another non-limiting formulation, the oxygen content is less than about 0.05 wt % of the novel alloy. In still another non-limiting formulation, the oxygen content is less than about 0.04 wt % of the novel alloy. In yet another non-limiting formulation, the oxygen content is less than about 0.03 wt % of the novel alloy. In still yet another non-limiting formulation, the novel alloy includes up to about 100 ppm oxygen. In a further non-limiting formulation, the novel alloy includes up to about 75 ppm oxygen. In still a further non-limiting formulation, the novel alloy includes up to about 50 ppm oxygen. In yet a further non-limiting formulation, the novel alloy includes up to about 30 ppm oxygen. In still yet a further non-limiting formulation, the novel alloy includes less than about 20 ppm oxygen. In yet a further non-limiting formulation, the novel alloy includes less than about 10 ppm oxygen. As can be appreciated, other amounts of carbon and/or oxygen in the novel alloy can exist. It is believed that the novel alloy will have a very low tendency to form micro-cracks during the formation of the medical device (e.g., medical device, etc.) and after the medical device has been inserted into a patient by closely controlling the carbon to oxygen ration when the oxygen content exceed a certain amount in the novel alloy. In one non-limiting arrangement, the carbon to oxygen atomic ratio in the novel alloy is at least about 2.5:1 when the oxygen content is greater than about 100 ppm in the novel alloy of the novel alloy.

In still yet another and/or alternative non-limiting aspect of the present invention, the novel alloy includes a controlled amount of nitrogen; however, this is not required. Large amounts of nitrogen in the novel alloy can adversely affect the ductility of the novel alloy. This can in turn adversely affect the elongation properties of the novel alloy. A too high of nitrogen content in the novel alloy can begin to cause the ductility of the novel alloy to unacceptably decrease, thus adversely affecting one or more physical properties of the novel alloy that are useful or desired in forming and/or using the medical device. In one non-limiting formulation, the novel alloy includes less than about 0.001 wt % nitrogen. In another non-limiting formulation, the novel alloy includes less than about 0.0008 wt % nitrogen. In still another non-limiting formulation, the novel alloy includes less than about 0.0004 wt % nitrogen. In yet another non-limiting formulation, the novel alloy includes less than about 30 ppm nitrogen. In still yet another non-limiting formulation, the novel alloy includes less than about 25 ppm nitrogen. In still another non-limiting formulation, the novel alloy includes less than about 10 ppm nitrogen. In yet another non-limiting formulation, the novel alloy of the novel alloy includes less than about 5 ppm nitrogen. As can be appreciated, other amounts of nitrogen in the novel alloy can exist.

The relationship of carbon, oxygen and nitrogen in the novel alloy is also important. It is believed that the nitrogen content should be less than the content of carbon or oxygen in the novel alloy. In one non-limiting formulation, the atomic ratio of carbon to nitrogen is at least about 2:1 (i.e., weight ratio of about 1.71:1). In another non-limiting formulation, the atomic ratio of carbon to nitrogen is at least about 3:1 (i.e., weight ratio of about 2.57:1). In still another non-limiting formulation, the atomic ratio of carbon to nitrogen is about 4-100:1 (i.e., weight ratio of about 3.43-85.7:1). In yet another non-limiting formulation, the atomic ratio of carbon to nitrogen is about 4-75:1 (i.e., weight ratio of about 3.43-64.3:1). In still another non-limiting formulation, the atomic ratio of carbon to nitrogen is about 4-50:1 (i.e., weight ratio of about 3.43-42.85:1). In yet another non-limiting formulation, the atomic ratio of carbon to nitrogen is about 4-35:1 (i.e., weight ratio of about 3.43-30:1). In still yet another non-limiting formulation, the atomic ratio of carbon to nitrogen is about 4-25:1 (i.e., weight ratio of about 3.43-21.43:1). In a further non-limiting formulation, the atomic ratio of oxygen to nitrogen is at least about 1.2:1 (i.e., weight ratio of about 1.37:1). In another non-limiting formulation, the atomic ratio of oxygen to nitrogen is at least about 2:1 (i.e., weight ratio of about 2.28:1). In still another non-limiting formulation, the atomic ratio of oxygen to nitrogen is about 3-100:1 (i.e., weight ratio of about 3.42-114.2:1). In yet another non-limiting formulation, the atomic ratio of oxygen to nitrogen is at least about 3-75:1 (i.e., weight ratio of about 3.42-85.65:1). In still yet another non-limiting formulation, the atomic ratio of oxygen to nitrogen is at least about 3-55:1 (i.e., weight ratio of about 3.42-62.81:1). In yet another non-limiting formulation, the atomic ratio of oxygen to nitrogen is at least about 3-50:1 (i.e., weight ratio of about 3.42-57.1:1).

In a further and/or alternative non-limiting aspect of the present invention, the novel alloy has several physical properties that positively affect the medical device when the medical device is at least partially formed of the novel alloy. In one non-limiting embodiment of the invention, the average Vickers hardness of the novel alloy tube used to form the medical device is generally at least about 234 DHP (i.e., Rockwell A hardness of at least about 60 at 77° F., Rockwell C hardness of at least about 19 at 77° F.); however, this is not required. In one non-limiting aspect of this embodiment, the average hardness of the novel alloy used to form the medical device is generally at least about 248 DHP (i.e., Rockwell A hardness of at least about 62 at 77° F., Rockwell C hardness of at least about 22 at 77° F.). In another and/or additional non-limiting aspect of this embodiment, the average hardness of the novel alloy used to form the medical device is generally about 248-513 DHP (i.e., Rockwell A hardness of about 62-76 at 77° F., Rockwell C hardness of about 22-50 at 77° F.). In still another and/or additional non-limiting aspect of this embodiment, the average hardness of the novel alloy used to form the medical device is generally about 272-458 DHP (i.e., Rockwell A hardness of about 64-74 at 77° F., Rockwell C hardness of about 26-46 at 77° F.). When titanium, yttrium and/or zirconium are included in an alloy of molybdenum and rhenium, the average hardness of the novel alloy is generally increased. Tungsten and tantalum alloys also generally have an average hardness of the novel alloy that is slightly greater than pure alloys of molybdenum and rhenium. In tungsten and tantalum alloys, and molybdenum and rhenium alloys that include titanium, yttrium and/or zirconium, the average hardness is generally at least about 60 (HRC) at 77° F., typically at least about 70 (HRC) at 77° F., and more typically about 80-100 (HRC) at 77° F. In another and/or alternative non-limiting embodiment of the invention, the average ultimate tensile strength of the novel alloy used to form the medical device is generally at least about 60 UTS (ksi); however, this is not required. In one non-limiting aspect of this embodiment, the average ultimate tensile strength of the novel alloy used to form the medical device is generally at least about 70 UTS (ksi), typically about 80-320 UTS (ksi), and more typically about 100-310 UTS (ksi). The average ultimate tensile strength of the novel alloy may vary somewhat when the novel alloy is in the form of a tube or a solid wire. When the novel alloy is in the form of a tube, the average ultimate tensile strength of the novel alloy tube is generally about 80-150 UTS (ksi), typically at least about 110 UTS (ksi), and more typically 110-140 UTS (ksi). When the novel alloy is in the form of a solid wire, the average ultimate tensile strength of the novel alloy wire is generally about 120-310 UTS (ksi). In still another and/or alternative non-limiting embodiment of the invention, the average yield strength of the novel alloy used to form the medical device is at least about 70 ksi; however, this is not required. In one non-limiting aspect of this embodiment, the average yield strength of the novel alloy used to form the medical device is at least about 80 ksi, and typically about 100-140 ksi. In yet another and/or alternative non-limiting embodiment of the invention, the average grain size of the novel alloy used to form the medical device is no greater than about 4 ASTM (e.g., ASTM 112-96); however, this is not required. The grain size as small as about 14-15 ASTM can be achieved; however, the grain size is typically larger than 15 ASTM. The small grain size of the novel alloy enables the medical device to have the desired elongation and ductility properties that are useful in enabling the medical device to be formed, crimped and/or expanded. In one non-limiting aspect of this embodiment, the average grain size of the novel alloy used to form the medical device is about 5.2-10 ASTM, typically about 5.5-9 ASTM, more typically about 6-9 ASTM, still more typically about 6-9 ASTM, even more typically about 6.6-9 ASTM, and still even more typically about 7-8.5 ASTM; however, this is not required.

In still yet another and/or alternative non-limiting embodiment of the invention, the average tensile elongation of the novel alloy used to form the medical device is at least about 25%. An average tensile elongation of at least 25% for the novel alloy is important to enable the medical device to be properly expanded when positioned in the treatment area of a body passageway. A medical device that does not have an average tensile elongation of at least about 25% can form micro-cracks and/or break during the forming, crimping and/or expansion of the medical device. In one non-limiting aspect of this embodiment, the average tensile elongation of the novel alloy used to form the medical device is about 25-35%. The unique combination of the rhenium and molybdenum or tungsten and tantalum in the novel alloy in combination with achieving the desired purity and composition of the alloy and the desired grain size of the novel alloy results in 1) a medical device having the desired high ductility at about room temperature, 2) a medical device having the desired amount of tensile elongation, 3) a homogeneous or solid solution of a novel alloy having high radiopacity, 4) a reduction or prevention of micro-crack formation and/or breaking of the novel alloy tube when the novel alloy tube is sized and/or cut to form the medical device, 5) a reduction or prevention of micro-crack formation and/or breaking of the medical device when the medical device is crimped onto a balloon and/or other type of medical device for insertion into a body passageway, 6) a reduction or prevention of micro-crack formation and/or breaking of the medical device when the medical device is bent and/or expanded in a body passageway, 7) a medical device having the desired ultimate tensile strength and yield strength, 8) a medical device that can have very thin wall thicknesses and still have the desired radial forces needed to retain the body passageway on an open state when the medical device has been expanded, and/or 9) a medical device that exhibits less recoil when the medical device is crimped onto a delivery system and/or expanded in a body passageway.

In still a further and/or alternative non-limiting aspect of the present invention, the novel alloy is at least partially formed by a swaging process; however, this is not required. In one non-limiting embodiment, the medical device includes one or more rods or tubes upon which swaging is performed to at least partially or fully achieve final dimensions of one or more portions of the medical device. The swaging dies can be shaped to fit the final dimension of the medical device; however, this is not required. Where there are undercuts of hollow structures in the medical device (which is not required), a separate piece of metal can be placed in the undercut to at least partially fill the gap. The separate piece of metal (when used) can be designed to be later removed from the undercut; however, this is not required. The swaging operation can be performed on the medical device in the areas to be hardened. For a round or curved portion of a medical device, the swaging can be rotary. For non-round portion of the medical device, the swaging of the non-round portion of the medical device can be performed by non-rotating swaging dies. The dies can optionally be made to oscillate in radial and/or longitudinal directions instead of or in addition to rotating. The medical device can optionally be swaged in multiple directions in a single operation or in multiple operations to achieve a hardness in desired location and/or direction of the medical device. The swaging temperature for a particular novel alloy (e.g., MoRe alloy, etc.) can vary. For a MoRe alloy, the swaging temperature can be from RT (e.g., 65-75° F.) to about 400° C. if the swaging is conducted in air or an oxidizing environment. The swaging temperature can be increased to up to about 1500° C. if the swaging process is performed in a controlled neutral or non-reducing environment (e.g., inert environment). The swaging process can be conducted by repeatedly hammering the medical device at the location to be hardened at the desired swaging temperature. In one non-limiting embodiment, during the swaging process ions of boron and/or nitrogen are allowed to impinge upon rhenium atoms in the MoRe alloy so as to form ReB2, ReN2 and/or ReN3; however, this is not required. It has been found that ReB2, ReN2 and/or ReN3 are ultra-hard compounds. In another and/or alternative non-limiting embodiment, all or a portion of the novel alloy coating (e.g., MoRe alloy coating) can be coated with another novel alloy (e.g., titanium alloy, etc.); however, this is not required. The coated novel alloy can have a hardness at RT that is greater than the hardness of the novel alloy in the core; however, this is not required. Generally, the coated alloy has a melting point that is less than the melting point of the material that forms the core; however, this is not required. For example, if the medical device is formed of MoRe, one or more portions of the MoRe implant can be coated by dipping in molten material such as titanium-5 alloy. Melting temperature of titanium-5 alloy is about 1660° C. and MoRe has a melting temperature of about 2450° C. Due to the higher melting temperature of MoRe, the coating of titanium-5 alloy on the MoRe results in the MoRe maintaining its shape after the coating process. In one non-limiting process, the metal for the medical device can be machined and shaped into the medical device when the metal is in a less hardened state. As such, the raw starting material can be first annealed to soften and then machined into the metal into a desired shape. After the novel alloy is shaped, the novel alloy can be re-hardened. The hardening of the metal material of the medical device can improve the wear resistance and/or shape retention of the medical device. The metal material of the medical generally cannot be re-hardened by annealing, thus a special rehardening processes is required. Such rehardening can be achieved by the swaging process of the present invention.

Several non-limiting examples of the metal alloy that can be made in accordance with the present invention are set forth below.

| Metal/wt % | Ex. 1 | Ex. 2 | Ex. 3 |
|---|---|---|---|
| C | <150 ppm | <50 ppm | <50 ppm |
| Mo | 51-54% | 52.5-55.5% | 50.5-52.4% |
| O | <50 ppm | <10 ppm | <10 ppm |
| N | <20 ppm | <10 ppm | <10 ppm |
| Re | 46-49% | 44.5-47.5% | 47.6-49.5% |

| Metal/wt % | Ex. 4 | Ex. 5 | Ex. 6 | Ex. 7 |
|---|---|---|---|---|
| C | ≤50 ppm | ≤50 ppm | ≤50 ppm | ≤50 ppm |
| Mo | 51-54% | 52.5-55.5% | 52-56% | 52.5-55% |
| O | ≤20 ppm | ≤20 ppm | ≤10 ppm | ≤10 ppm |
| N | ≤20 ppm | ≤20 ppm | ≤10 ppm | ≤10 ppm |
| Re | 46-49% | 44.5-47.5% | 44-48% | 45-47.5% |
| Ti | ≤0.4% | ≤0.4% | 0.2-0.4% | 0.3-0.4% |
| Y | ≤0.1% | ≤0.1% | 0-0.08% | 0.005-05% |
| Zr | ≤0.2% | ≤0.2% | 0-0.2% | 0.1-0.25% |

| Metal/wt % | Ex. 8 | Ex. 9 | Ex. 10 | Ex. 11 |
|---|---|---|---|---|
| C | ≤40 ppm | ≤40 ppm | ≤40 ppm | ≤40 ppm |
| Mo | 50.5-53% | 51.5-54% | 52-55% | 52.5-55% |
| O | ≤15 ppm | ≤15 ppm | ≤15 ppm | ≤10 ppm |
| N | ≤10 ppm | ≤10 ppm | ≤10 ppm | ≤10 ppm |
| Re | 47-49.5% | 46-48.5% | 45-48% | 45-47.5% |
| Ti | 0.1-0.35% | 0% | 0% | 0.1-0.3% |
| Y | 0% | 0.002-0.08% | 0% | 0% |
| Zr | 0% | 0% | 00.1-0.2% | 0.05-.15% |

| Metal/wt % | Ex. 12 | Ex. 13 | Ex. 14 | Ex. 15 |
|---|---|---|---|---|
| C | ≤40 ppm | ≤40 ppm | <150 ppm | <150 ppm |
| Mo | 52-55% | 52.5-55.5% | 50-60% | 50-60% |
| O | ≤10 ppm | ≤10 ppm | ≤100 ppm | ≤100 ppm |
| N | ≤10 ppm | ≤10 ppm | ≤40 ppm | ≤40 ppm |
| Re | 45-49% | 44.5-47.5% | 40-50% | 40-50% |
| Ti | 0.05-0.4% | 0% | 0% | ≤1% |
| Y | 0.005-0.07% | 0.004-0.06% | 0% | ≤0.1% |
| Zr | 0% | 0.1-0.2% | 0% | ≤2% |

| Metal/wt % | Ex. 16 | Ex. 17 | Ex. 18 | Ex. 19 |
|---|---|---|---|---|
| C | ≤150 ppm | ≤150 ppm | ≤150 ppm | ≤150 ppm |
| Mo | 50-55% | 52-55.5% | 51-58% | 50-56% |
| O | ≤100 ppm | ≤100 ppm | ≤100 ppm | ≤100 ppm |
| N | ≤40 ppm | ≤20 ppm | ≤20 ppm | ≤20 ppm |

-continued

| Metal/wt % | | | |
|---|---|---|---|
| Re | 45-50% | 44.5-48% | 42-49% | 44-50% |
| Ti | 0% | 0% | 0% | 0% |
| Y | 0% | 0% | 0% | 0% |
| Zr | 0% | 0% | 0% | 0% |

| Metal/wt % | Ex. 20 | Ex. 21 | Ex. 22 |
|---|---|---|---|
| C | <150 ppm | <50 ppm | <50 ppm |
| Mo | 51-54% | 52.5-55.5% | 50.5-52.4% |
| O | <50 ppm | <10 ppm | <10 ppm |
| N | <20 ppm | <10 ppm | <10 ppm |
| Re | 46-49% | 44.5-47.5% | 47.6-49.5% |
| Ti | 0% | 0% | 0% |
| Y | 0% | 0% | 0% |
| Zr | 0% | 0% | 0% |

| Metal/wt % | Ex. 23 | Ex. 24 | Ex. 25 |
|---|---|---|---|
| C | ≤150 ppm | ≤150 ppm | ≤150 ppm |
| Mo | 50-60% | 50-60% | 50-55% |
| O | ≤100 ppm | ≤100 ppm | ≤100 ppm |
| N | ≤40 ppm | ≤40 ppm | ≤40 ppm |
| Re | 40-50% | 40-50% | 45-50% |
| Ti | ≤0.5% | ≤0.5% | ≤0.5% |
| Y | ≤0.1% | ≤0.1% | ≤0.1% |
| Zr | ≤0.25% | ≤0.25% | ≤0.25% |

| Metal/wt % | Ex. 26 | Ex. 27 | Ex. 28 |
|---|---|---|---|
| C | ≤150 ppm | ≤150 ppm | ≤150 ppm |
| Mo | 52-55.5% | 51-58% | 50-56% |
| O | ≤100 ppm | ≤100 ppm | ≤100 ppm |
| N | ≤20 ppm | ≤20 ppm | ≤20 ppm |
| Re | 44.5-48% | 42-49% | 44-50% |
| Ti | ≤0.5% | ≤0.5% | ≤0.5% |
| Y | ≤0.1% | ≤0.1% | ≤0.1% |
| Zr | ≤0.25% | ≤0.25% | ≤0.25% |

| Metal/wt % | Ex. 29 | Ex. 30 | Ex. 31 | Ex. 32 |
|---|---|---|---|---|
| C | ≤50 ppm | ≤50 ppm | ≤50 ppm | ≤50 ppm |
| Mo | 51-54% | 52.5-55.5% | 52-56% | 52.5-55% |
| O | ≤20 ppm | ≤20 ppm | ≤10 ppm | ≤10 ppm |
| N | ≤20 ppm | ≤20 ppm | ≤10 ppm | ≤10 ppm |
| Re | 46-49% | 44.5-47.5% | 44-48% | 45-47.5% |
| Ti | ≤0.4% | ≤0.4% | 0.2-0.4% | 0.3-0.4% |
| Y | ≤0.1% | ≤0.1% | 0-0.08% | 0.005-0.05% |
| Zr | ≤0.2% | ≤0.2% | 0-0.2% | 0.1-0.25% |

| Metal/wt % | Ex. 33 | Ex. 34 | Ex. 35 | Ex. 36 |
|---|---|---|---|---|
| C | ≤40 ppm | ≤40 ppm | ≤40 ppm | ≤40 ppm |
| Mo | 50.5-53% | 51.5-54% | 52-55% | 52.5-55% |
| O | ≤15 ppm | ≤15 ppm | ≤15 ppm | ≤10 ppm |
| N | ≤10 ppm | ≤10 ppm | ≤10 ppm | ≤10 ppm |
| Re | 47-49.5% | 46-48.5% | 45-48% | 45-47.5% |
| Ti | 0.1-0.35% | 0% | 0% | 0.1-0.3% |
| Y | 0% | 0.002-0.08% | 0% | 0% |
| Zr | 0% | 0% | 0.01-0.2% | 0.05-.15% |

| Metal/wt % | Ex. 37 | Ex. 38 |
|---|---|---|
| C | ≤40 ppm | ≤40 ppm |
| Mo | 52-55% | 52.5-55.5% |
| O | ≤10 ppm | ≤10 ppm |
| N | ≤10 ppm | ≤10 ppm |
| Re | 45-49% | 44.5-47.5% |
| Ti | 0.05-0.4% | 0% |
| Y | 0.005-0.07% | 0.004-0.06% |
| Zr | 0% | 0.1-0.2% |

| Metal/wt % | Ex. 39 |
|---|---|
| C | ≤150 ppm |
| Mo | 50-60% |
| O | ≤100 ppm |
| N | ≤40 ppm |
| Nb | ≤5% |
| Rare Earth Metal | ≤4% |
| Re | 40-50% |
| Ta | ≤3% |
| Ti | ≤1% |
| W | ≤3% |
| Y | ≤0.1% |
| Zn | ≤0.1% |
| Zr | ≤2% |

| Metal/wt % | Ex. 40 |
|---|---|
| C | ≤0.01% |
| Co | ≤0.002% |
| Fe | ≤0.02% |
| H | ≤0.002% |
| Mo | 52-53% |
| N | ≤0.0008% |
| Ni | ≤0.01% |
| O | ≤0.06% |
| Re | 47-48% |
| S | ≤0.008% |
| Sn | ≤0.002% |
| Ti | ≤0.002% |
| W | ≤0.02% |

| Metal/wt % | Ex. 41 | Ex. 42 | Ex. 43 | Ex. 44 |
|---|---|---|---|---|
| C | 0-50 ppm | 0-50 ppm | 0-50 ppm | 0-50 ppm |
| Ca | 0-1% | 0-0.5% | 0% | 0% |
| Mg | 0% | 0-3% | 0% | 0% |
| Mo | 0% | 0-2% | 0% | 0% |
| O | 0-50 ppm | 0-50 ppm | 0-50 ppm | 0-50 ppm |
| N | 0-50 ppm | 0-50 ppm | 0-50 ppm | 0-50 ppm |
| Rare Earth Metal | 0-1% | 0-0.5% | 0% | 0% |
| Re | 0-6% | 0-5% | 0-4% | 0% |
| Ta | 85-96% | 10-90% | 85-95% | 90.5-98% |
| W | 4-15% | 10-90% | 5-15% | 2-9.5% |
| Y | 0% | 0-1% | 0% | 0% |
| Zn | 0% | 0-1% | 0% | 0% |
| Zr | 0% | 0-1% | 0% | 0% |

| Metal/wt % | Ex. 45 | Ex. 46 |
|---|---|---|
| C | 0-50 ppm | 0-50 ppm |
| Ca | 0% | 0% |
| Mg | 0% | 0% |
| Mo | 0% | 0% |
| O | 0-50 ppm | 0-50 ppm |
| N | 0-50 ppm | 0-50 ppm |
| Rare Earth Metal | 0% | 0% |
| Re | 0-4% | 0% |
| Ta | 95-98% | 90-97.5% |
| W | 2% to less than 5% | 2.5-10% |
| Y | 0% | 0% |
| Zn | 0% | 0% |
| Zr | 0% | 0% |

In Examples 1-3, 14, 16-19, and 20-22 above, the metal alloy is principally formed of rhenium and molybdenum and the content of other metals and/or impurities is less than about 0.1 wt % of the metal alloy, the atomic ratio of carbon to oxygen is about 2.5-10:1 (i.e., weight ratio of about 1.88-7.5:1), the average grain size of the metal alloy is about 6-10 ASTM, the tensile elongation of the metal alloy is about 25-35%, the average density of the metal alloy is at least about 13.4 gm/cc, the average yield strength of the metal alloy is about 98-122 (ksi), the average ultimate tensile strength of the metal alloy is about 150-310 UTS (ksi), and an average Vickers hardness of 372-653 (i.e., Rockwell A Hardness of about 70-80 at 77° F., an average Rockwell C Hardness of about 39-58 at 77° F.). In Examples 4-7, 8-11, 12, 13, 15, and 32-38 above, the metal alloy is principally formed of rhenium and molybdenum and at least one metal of titanium, yttrium and/or zirconium, and the content of other metals and/or impurities is less than about 0.1 wt % of the metal alloy, the ratio of carbon to oxygen is about 2.5-10:1, the average grain size of the metal alloy is about 6-10 ASTM, the tensile elongation of the metal alloy is about 25-35%, the average density of the metal alloy is at least about 13.6 gm/cc, the average yield strength of the metal alloy is at least about 110 (ksi), the average ultimate tensile strength of the metal alloy is about 150-310 UTS (ksi), and an average Vickers hardness of 372-653 (i.e., an average Rockwell A Hardness of about 70-80 at 77° F., an average Rockwell C Hardness of about 39-58 at 77° F.). The remaining alloys identified in the above Examples may or may not include titanium, yttrium and/or zirconium. The properties of these alloys will be similar to the alloys discussed in the above Examples. In Example 32, the weight ratio of titanium to zirconium is about 1.5-3:1. In Example 36, the weight ratio of titanium to zirconium is about 1.75-2.5:1. In Examples 29-32, the weight ratio of titanium to zirconium is about 1-10:1. In Example 40, the ratio of carbon to oxygen is at least about 0.4:1 (i.e., weight ratio of carbon to oxygen of at least about 0.3:1), the nitrogen content is less than the carbon content and the oxygen content, the atomic ratio of carbon to nitrogen is at least about 4:1 (i.e., weight ratio of about 3.43:1), the atomic ratio of oxygen to nitrogen is at least about 3:1 (i.e., weight ratio of about 3.42:1), the average grain size of metal alloy is about 6-10 ASTM, the tensile elongation of the metal alloy is about 25-35%, the average density of the metal alloy is at least about 13.4 gm/cc, the average yield strength of the metal alloy is about 98-122 (ksi), the average ultimate tensile strength of the metal alloy is about 100-150 UTS (ksi), and the average hardness of the metal alloy is about 80-100 (HRC) at 77° F.

In Examples 41-46, the metal alloy is principally formed of tungsten and tantalum and the content of other metals and/or impurities is less than about 0.1 wt %, and typically less than 0.04 wt % of the metal alloy.

| Metal/wt % | Ex. 47 | Ex. 48 | Ex. 49 |
|---|---|---|---|
| C | <150 ppm | <50 ppm | <50 ppm |
| Mo | 51-54% | 52.5-55.5% | 50.5-52.4% |
| O | <50 ppm | <10 ppm | <10 ppm |
| N | <20 ppm | <10 ppm | <10 ppm |
| Re | 46-49% | 44.5-47.5% | 47.6-49.5% |
| CNT | 0.05-10% | 0.05-10% | 0.05-10% |

| Metal/wt % | Ex. 50 | Ex. 51 | Ex. 52 | Ex. 53 |
|---|---|---|---|---|
| C | ≤50 ppm | ≤50 ppm | ≤50 ppm | ≤50 ppm |
| Mo | 51-54% | 52.5-55.5% | 52-56% | 52.5-55% |
| O | ≤20 ppm | ≤20 ppm | ≤10 ppm | ≤10 ppm |
| N | ≤20 ppm | ≤20 ppm | ≤10 ppm | ≤10 ppm |
| Re | 46-49% | 44.5-47.5% | 44-48% | 45-47.5% |
| CNT | 0.1-8% | 0.1-8% | 0.1-8% | 0.1-8% |

| Metal/wt % | Ex. 55 | Ex. 555 | Ex. 56 | Ex. 57 |
|---|---|---|---|---|
| C | ≤40 ppm | ≤40 ppm | ≤40 ppm | ≤40 ppm |
| Mo | 50.5-53% | 51.5-54% | 52-55% | 52.5-55% |
| O | ≤15 ppm | ≤15 ppm | ≤15 ppm | ≤10 ppm |
| N | ≤10 ppm | ≤10 ppm | ≤10 ppm | ≤10 ppm |
| Re | 47-49.5% | 46-48.5% | 45-48% | 45-47.5% |
| CNT | 0.1-8% | 0.1-8% | 0.1-8% | 0.1-8% |

| Metal/wt % | Ex. 58 | Ex. 59 | Ex. 60 | Ex. 61 |
|---|---|---|---|---|
| C | ≤40 ppm | ≤40 ppm | <150 ppm | <150 ppm |
| Mo | 52-55% | 52.5-55.5% | 50-60% | 50-60% |
| O | ≤10 ppm | ≤10 ppm | ≤100 ppm | ≤100 ppm |
| N | ≤10 ppm | ≤10 ppm | ≤40 ppm | ≤40 ppm |
| Re | 45-49% | 44.5-47.5% | 40-50% | 40-50% |
| CNT | 0.1-8% | 0.1-8% | 0.1-8% | 0.1-8% |

| Metal/wt % | Ex. 62 | Ex. 63 | Ex. 64 | Ex. 65 |
|---|---|---|---|---|
| C | ≤150 ppm | ≤150 ppm | ≤150 ppm | ≤150 ppm |
| Mo | 50-55% | 52-55.5% | 51-58% | 50-56% |
| O | ≤100 ppm | ≤100 ppm | ≤100 ppm | ≤100 ppm |
| N | ≤40 ppm | ≤20 ppm | ≤20 ppm | ≤20 ppm |
| Re | 45-50% | 44.5-48% | 42-49% | 44-50% |
| CNT | 0.1-8% | 0.1-8% | 0.1-8% | 0.1-8% |

| Metal/wt % | Ex. 66 | Ex. 67 | Ex. 68 |
|---|---|---|---|
| C | <150 ppm | <50 ppm | <50 ppm |
| Mo | 51-54% | 52.5-55.5% | 50.5-52.4% |
| O | <50 ppm | <10 ppm | <10 ppm |
| N | <20 ppm | <10 ppm | <10 ppm |
| Re | 46-49% | 44.5-47.5% | 47.6-49.5% |
| CNT | 0.1-8% | 0.1-8% | 0.1-8% |

| Metal/wt % | Ex. 69 | Ex. 70 | Ex. 71 |
|---|---|---|---|
| C | ≤150 ppm | ≤150 ppm | ≤150 ppm |
| Mo | 50-60% | 50-60% | 50-55% |
| O | ≤100 ppm | ≤100 ppm | ≤100 ppm |
| N | ≤40 ppm | ≤40 ppm | ≤40 ppm |
| Re | 40-50% | 40-50% | 45-50% |
| CNT | 0.5-5% | 0.5-5% | 0.5-5% |

| Metal/wt % | Ex. 72 | Ex. 73 | Ex. 74 |
|---|---|---|---|
| C | ≤150 ppm | ≤150 ppm | ≤150 ppm |
| Mo | 52-55.5% | 51-58% | 50-56% |
| O | ≤100 ppm | ≤100 ppm | ≤100 ppm |
| N | ≤20 ppm | ≤20 ppm | ≤20 ppm |
| Re | 44.5-48% | 42-49% | 44-50% |
| CNT | 0.5-5% | 0.5-5% | 0.5-5% |

| Metal/wt % | Ex. 75 | Ex. 76 | Ex. 77 | Ex. 78 |
|---|---|---|---|---|
| C | ≤50 ppm | ≤50 ppm | ≤50 ppm | ≤50 ppm |
| Mo | 51-54% | 52.5-55.5% | 52-56% | 52.5-55% |
| O | ≤20 ppm | ≤20 ppm | ≤10 ppm | ≤10 ppm |
| N | ≤20 ppm | ≤20 ppm | ≤10 ppm | ≤10 ppm |
| Re | 46-49% | 44.5-47.5% | 44-48% | 45-47.5% |
| CNT | 0.5-5% | 0.5-5% | 0.5-5% | 0.5-5% |

| Metal/wt % | Ex. 79 | Ex. 80 | Ex. 81 | Ex. 82 |
|---|---|---|---|---|
| C | ≤40 ppm | ≤40 ppm | ≤40 ppm | ≤40 ppm |
| Mo | 50.5-53% | 51.5-54% | 52-55% | 52.5-55% |
| O | ≤15 ppm | ≤15 ppm | ≤15 ppm | ≤10 ppm |
| N | ≤10 ppm | ≤10 ppm | ≤10 ppm | ≤10 ppm |
| Re | 47-49.5% | 46-48.5% | 45-48% | 45-47.5% |
| CNT | 0.5-5% | 0.5-5% | 0.5-5% | 0.5-5% |

| Metal/wt % | Ex. 83 | Ex. 84 |
|---|---|---|
| C | ≤40 ppm | ≤40 ppm |
| Mo | 52-55% | 52.5-55.5% |
| O | ≤10 ppm | ≤10 ppm |
| N | ≤10 ppm | ≤10 ppm |
| Re | 45-49% | 44.5-47.5% |
| CNT | 0.5-5% | 0.5-5% |

| Metal/wt % | Ex. 85 |
|---|---|
| C | ≤150 ppm |
| Hf | ≤5% |
| Mo | 20-90% |
| O | ≤100 ppm |
| Os | ≤5% |
| N | ≤40 ppm |
| Nb | ≤5% |
| Pt | ≤5% |
| Rare Earth Metal | ≤4% |
| Re | 10-80% |
| Ta | ≤3% |
| Tc | ≤5% |
| Ti | ≤1% |

-continued

| Metal/wt % | Ex. 85 (cont.) |
|---|---|
| V | ≤5% |
| W | ≤3% |
| Y | ≤0.1% |
| Zn | ≤0.1% |
| Zr | ≤5% |
| CNT | 0.05-10% |

| Metal/wt % | Ex. 86 |
|---|---|
| C | ≤0.01% |
| Co | ≤0.002% |
| Fe | ≤0.02% |
| H | ≤0.002% |
| Hf | ≤1% |
| Mo | 40-90% |
| N | ≤0.0008% |
| Nb | ≤1% |
| Ni | ≤0.01% |
| O | ≤0.06% |
| Os | ≤1% |
| Pt | ≤1% |
| Re | 10-60% |
| S | ≤0.008% |
| Sn | ≤0.002% |
| Tc | ≤1% |
| Ti | ≤1% |
| V | ≤1% |
| W | ≤1% |
| Zr | ≤1% |
| CNT | 0.5-5% |

| Metal/wt % | Ex. 87 |
|---|---|
| C | ≤150 ppm |
| Hf | ≤5% |
| Mo | 20-80% |
| O | ≤100 ppm |
| Os | ≤5% |
| N | ≤40 ppm |
| Nb | ≤5% |
| Pt | ≤5% |
| Rare Earth Metal | ≤4% |
| Re | 20-80% |
| Ta | ≤3% |

-continued

| Metal/wt % | Ex. 87 (cont.) |
|---|---|
| Tc | ≤5% |
| Ti | ≤1% |
| V | ≤5% |
| W | ≤3% |
| Y | ≤0.1% |
| Zn | ≤0.1% |
| Zr | ≤5% |

| Metal/wt % | Ex. 88 |
|---|---|
| C | ≤0.01% |
| Co | ≤0.002% |
| Fe | ≤0.02% |
| H | ≤0.002% |
| Hf | ≤1% |
| Mo | 40-60% |
| N | ≤0.0008% |
| Nb | ≤1% |
| Ni | ≤0.01% |
| O | ≤0.06% |
| Os | ≤1% |
| Pt | ≤1% |
| Re | 40-60% |
| S | ≤0.008% |
| Sn | ≤0.002% |
| Tc | ≤1% |
| Ti | ≤1% |
| V | ≤1% |
| W | ≤1% |
| Zr | ≤1% |

In the examples above, the atomic ratio of carbon to oxygen can be about 2.5-10:1 (i.e., weight ratio of about 1.88-7.5:1), the average grain size of the novel alloy can be about 6-10 ASTM, the tensile elongation of the novel alloy can be about 25-35%, the average density of the novel alloy can be at least about 13.4 gm/cc, the average yield strength of the novel alloy can be about 98-122 (ksi), the average ultimate tensile strength of the novel alloy can be about 150-310 UTS (ksi), and an average Vickers hardness can be 372-653 (i.e., Rockwell A Hardness of about 70-80 at 77° F., an average Rockwell C Hardness of about 39-58 at 77° F.).

| Metal/wt % | Ex. 89 | Ex. 90 | Ex. 92 | Ex. 92 |
|---|---|---|---|---|
| Mo | 40-99.89% | 40-99.9% | 40-99.89% | 40-99.5% |
| C | 0.01-0.3% | 0-0.3% | 0-0.3% | 0-0.3% |
| Co | ≤0.002% | ≤0.002% | ≤0.002% | ≤0.002% |
| Ce₂O | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | ≤1% | ≤1% | ≤1% |
| La₂O₃ | 0-2% | 0.1-2% | 0-2% | 0-2% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 0-40% | 0-40% | 0-40% | 0-40% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| Y₂O₃ | 0-1% | 0-1% | 0.1-1% | 0-1% |
| Zr | ≤1% | ≤1% | ≤1% | ≤1% |
| ZrO₂ | 0-3% | 0-3% | 0-3% | 0-3% |
| CNT | 0-10% | 0-10% | 0-10% | 0-10% |

| Metal/wt % | Ex. 93 | Ex. 94 | Ex. 95 |
|---|---|---|---|
| Mo | 40-99.9% | 40-99.5% | 40-99.5% |
| C | 0-0.3% | 0-0.3% | 0-0.3% |

-continued

| | | | |
|---|---|---|---|
| Co | ≤0.002% | ≤0.002% | ≤0.002% |
| Ce₂O | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| La₂O₃ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 0-40% | 0-40% | 0.5-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| Y₂O₃ | 0-1% | 0-1% | 0-1% |
| ZrO₂ | 0.1-3% | 0-3% | 0-3% |
| CNT | 0-10% | 0-10% | 0-10% |

| Metal/wt % | Ex. 96 | Ex. 97 | Ex. 98 | Ex. 99 |
|---|---|---|---|---|
| Mo | 98-99.15% | 98-99.7% | 50-99.66% | 40-80% |
| C | 0.05-0.15% | 0-0.15% | 0-0.15% | 0-0.15% |
| Ce₂O | 0-0.2% | 0-0.2% | 0.04-0.1% | 0-0.2% |
| Hf | 0.8-1.4% | 0-2.5% | 0-2.5% | 0-2.5% |
| La₂O₃ | 0-2% | 0.3-0.7% | 0-2% | 0-2% |
| Re | 0-40% | 0-40% | 0-40% | 0-40% |
| Ta | 0-50% | 0-50% | 0-50% | 0-50% |
| W | 0-50% | 0-50% | 0-50% | 20-50% |
| Y₂O₃ | 0-1% | 0-1% | 0.3-0.5% | 0-1% |
| ZrO₂ | 0-3% | 0-3% | 0-3% | 0-3% |

| Metal/wt % | Ex. 100 | Ex. 101 | Ex. 102 |
|---|---|---|---|
| Mo | 97-98.8% | 50-90% | 60-99.5% |
| C | 0-0.15% | 0-0.15% | 0-0.15% |
| Ce₂O | 0-0.2% | 0-0.2% | 0-0.2% |
| Hf | 0-2.5% | 0-2.5% | 0-2.5% |
| La₂O₃ | 0-2% | 0-2% | 0-2% |
| Re | 0-40% | 0-40% | 5-40% |
| Ta | 0-50% | 10-50% | 0-50% |
| W | 0-50% | 0-50% | 0-50% |
| Y₂O₃ | 0-1% | 0-1% | 0-1% |
| ZrO₂ | 1.2-1.8% | 0-3% | 0-3% |

In Examples 89-102, it will be appreciated that all of the above ranges include and value between the range and other range that is between the range as set forth above. In the above metal alloys, the average grain size of the metal alloy can be about 6-10 ASTM, the tensile elongation of the metal alloy can be about 25-35%, the average density of the metal alloy can be at least about 13.4 gm/cc, the average yield strength of the metal alloy can be about 98-122 (ksi), the average ultimate tensile strength of the metal alloy can be about 100-310 UTS (ksi), an average Vickers hardness of 372-653 (i.e., Rockwell A Hardness can be about 70-100 at 77° F., an average Rockwell C Hardness can be about 39-58 at 77° F., the primarily tensile strength is over 1000 MPa, elongation is >10%; and modulus of elasticity is >300 GPa; however, this is not required.

In another and/or alternative non-limiting aspect of the present invention, the use of the metal alloy in the medical device can increase the strength of the medical device as compared with stainless steel or chromium-cobalt alloys, thus less quantity of metal alloy can be used in the medical device to achieve similar strengths as compared to medical devices formed of different metals. As such, the resulting medical device can be made smaller and less bulky by use of the metal alloy without sacrificing the strength and durability of the medical device. Such a medical device can have a smaller profile, thus can be inserted in smaller areas, openings and/or passageways. The metal alloy also can increase the radial strength of the medical device. For instance, the thickness of the walls of the medical device and/or the wires used to form the medical device can be made thinner and achieve a similar or improved radial strength as compared with thicker walled medical devices formed of stainless steel or cobalt-chromium alloy. The metal alloy also can improve stress-strain properties, bendability and flexibility of the medical device, thus increase the life of the medical device. For instance, the medical device can be used in regions that subject the medical device to bending. Due to the improved physical properties of the medical device from the metal alloy, the medical device has improved resistance to fracturing in such frequent bending environments. In addition or alternatively, the improved bendability and flexibility of the medical device due to the use of the metal alloy can enable the medical device to be more easily inserted into various regions of a body. The metal alloy can also reduce the degree of recoil during the crimping and/or expansion of the medical device. For example, the medical device better maintains its crimped form and/or better maintains its expanded form after expansion due to the use of the metal alloy. As such, when the medical device is to be mounted onto a delivery device when the medical device is crimped, the medical device better maintains its smaller profile during the insertion of the medical device in various regions of a body. Also, the medical device better maintains its expanded profile after expansion so as to facilitate in the success of the medical device in the treatment area. In addition to the improved physical properties of the medical device by use of the metal alloy, the metal alloy has improved radiopaque properties as compared to standard materials such as stainless steel or cobalt-chromium alloy, thus reducing or eliminating the need for using marker materials on the medical device. For instance, the metal alloy is believed to at least about 10-20% more radiopaque than stainless steel or cobalt-chromium alloy. Specifically, the metal alloy is believed to be at least about 33% more radiopaque than cobalt-chromium alloy and is believed to be at least about 41.5% more radiopaque than stainless steel.

In a further and/or alternative non-limiting aspect of the invention, the medical device can include a bistable construction. In such a design, the medical device has two or more stable configurations, including a first stable configuration with a first cross-sectional shape and a second stable configuration with a second cross-sectional shape. All or a portion of the medical device can include the bistable construction. The bistable construction can result in a generally uniform change in shape of the medical device, or one portion of the medical device can change into one or more configurations and one or more other portions of the medical device can change into one or more other configurations.

In yet another and/or alternative non-limiting aspect of the present invention, the medical device can include, contain and/or be coated with one or more agents that facilitate in the success of the medical device and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to viral, fungus and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. Non-limiting examples of agents that can be used include, but are not limited to, 5-fluorouracil and/or derivatives thereof; 5-phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca^{2+}$ transport such as L-type (e.g., diltiazem, nifedipine, verapamil, etc.) or T-type $Ca^{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; antibiotics; anti-coagulant compounds and/or derivatives thereof; anti-fibrosis compounds and/or derivatives thereof; antifungal compounds and/or derivatives thereof; anti-inflammatory compounds and/or derivatives thereof; anti-invasive factor and/or derivatives thereof; anti-metabolite compounds and/or derivatives thereof (e.g., staurosporin, trichothecenes, and modified diphtheria and ricin toxins, pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca^{2+}$/calmodulin kinase II, casein kinase II, etc.); aspirin and/or derivatives thereof; azathioprine and/or derivatives thereof; $-estradiol and/or derivatives thereof; $\beta$-1-anticollagenase and/or derivatives thereof; calcium channel blockers and/or derivatives thereof; calmodulin antagonists and/or derivatives thereof (e.g., H7, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the IP3 receptor and/or derivatives thereof; inhibitors of the sodium/hydrogen antiporter and/or derivatives thereof (e.g., amiloride and derivatives thereof, etc.); insulin and/or derivatives thereof; interferon α-2-macroglobulin and/or derivatives thereof; ketoconazole and/or derivatives thereof; lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; plasminogen activator inhibitor-1 and/or derivatives thereof; plasminogen activator inhibitor-2 and/or derivatives thereof; platelet factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, H3P3204, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; TH1 and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anticoagulant peptide and/or derivatives thereof; thioprotese inhibitors and/or derivatives thereof; thyroid hormone and/or derivatives thereof; tissue inhibitor of metalloproteinase-1 and/or derivatives thereof; tissue inhibitor of metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the agent can include one or more derivatives of the above listed compounds and/or other compounds. In one non-limiting embodiment, the agent includes, but is not limited to, trapidil, trapidil derivatives, taxol, taxol derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-phenylmethimazole, 5-phenylmethimazole derivatives, GM-CSF (granulo-cytemacrophage colony-stimulating-factor), GM-CSF derivatives, statins or HMG-CoA reductase inhibitors forming a class of hypolipidemic agents, combinations, or analogs thereof, or combinations thereof. The type and/or amount of agent included in the device and/or coated on the device can vary. When two or more agents are included in and/or coated on the device, the amount of two or more agents can be the same or different. The type and/or amount of agent included on, in and/or in conjunction with the device are generally selected to address one or more clinical events.

Typically, the amount of agent included on, in and/or used in conjunction with the device is about 0.01-100 ug per mm$^2$ and/or at least about 0.01 wt % of device; however, other amounts can be used. In one non-limiting embodiment of the invention, the device can be partially of fully coated and/or impregnated with one or more agents to facilitate in the success of a particular medical procedure. The amount of two or more agents on, in and/or used in conjunction with the device can be the same or different. The one or more agents can be coated on and/or impregnated in the device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition. In another and/or alternative non-limiting embodiment of the invention, the type and/or amount of agent included on, in and/or in conjunction with the device is generally selected for the treatment of one or more clinical events. Typically, the amount of agent included on, in and/or used in conjunction with the device is about 0.01-100 ug per $mm^2$ and/or at least about 0.01-100 wt % of the device; however, other amounts can be used. The amount of two of more agents on, in and/or used in conjunction with the device can be the same or different. As such, the medical device, when it includes, contains, and/or is coated with one or more agents, can include one or more agents to address one or more medical needs. In one non-limiting embodiment of the invention, the medical device can be partially or fully coated with one or more agents and/or impregnated with one or more agents to facilitate in the success of a particular medical procedure. The one or more agents can be coated on and/or impregnated in the medical device by a variety of mechanisms such as, but not limited to, spraying (e.g., atomizing spray techniques, etc.), dip coating, roll coating, sonication, brushing, plasma deposition, depositing by vapor deposition. In another and/or alternative non-limiting embodiment of the invention, the type and/or amount of agent included on, in and/or in conjunction with the medical device is generally selected for the treatment of one or more medical treatments. Typically, the amount of agent included on, in and/or used in conjunction with the medical device is about 0.01-100 ug per $mm^2$; however, other amounts can be used. The amount of two or more agents on, in and/or used in conjunction with the medical device can be the same or different.

In a further and/or alternative non-limiting aspect of the present invention, the one or more agents on and/or in the medical device, when used on the medical device, can be released in a controlled manner so the area in question to be treated is provided with the desired dosage of agent over a sustained period of time. As can be appreciated, controlled release of one or more agents on the medical device is not always required and/or desirable. As such, one or more of the agents on and/or in the medical device can be uncontrollably released from the medical device during and/or after insertion of the medical device in the treatment area. It can also be appreciated that one or more agents on and/or in the medical device can be controllably released from the medical device and one or more agents on and/or in the medical device can be uncontrollably released from the medical device. It can also be appreciated that one or more agents on and/or in one region of the medical device can be controllably released from the medical device and one or more agents on and/or in the medical device can be uncontrollably released from another region on the medical device. As such, the medical device can be designed such that 1) all the agent on and/or in the medical device is controllably released, 2) some of the agent on and/or in the medical device is controllably released and some of the agent on the medical device is non-controllably released, or 3) none of the agent on and/or in the medical device is controllably released. The medical device can also be designed such that the rate of release of the one or more agents from the medical device is the same or different. The medical device can also be designed such that the rate of release of the one or more agents from one or more regions on the medical device is the same or different. Non-limiting arrangements that can be used to control the release of one or more agents from the medical device include 1) at least partially coat one or more agents with one or more polymers, 2) at least partially incorporate and/or at least partially encapsulate one or more agents into and/or with one or more polymers, and/or 3) insert one or more agents in pores, passageway, cavities, etc. in the medical device and at least partially coat or cover such pores, passageway, cavities, etc. with one or more polymers. As can be appreciated, other or additional arrangements can be used to control the release of one or more agents from the medical device.

The one or more polymers used to at least partially control the release of one or more agents from the medical device can be porous or non-porous. The one or more agents can be inserted into and/or applied to one or more surface structures and/or micro-structures on the medical device, and/or be used to at least partially form one or more surface structures and/or micro-structures on the medical device. As such, the one or more agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more agents are coated on the medical device, the one or more agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials.

As can be appreciated, many other coating arrangements can be additionally or alternatively used. When the one or more agents are inserted and/or impregnated in one or more internal structures, surface structures and/or micro-structures of the medical device, 1) one or more other coating materials can be applied at least partially over the one or more internal structures, surface structures and/or micro-structures of the medical device, and/or 2) one or more polymers can be combined with one or more agents. As such, the one or more agents can be 1) embedded in the structure of the medical device; 2) positioned in one or more internal structures of the medical device; 3) encapsulated between two polymer coatings; 4) encapsulated between the base structure and a polymer coating; 5) mixed in the base structure of the medical device that includes at least one polymer coating; or 6) one or more combinations of 1, 2, 3, 4 and/or 5. In addition or alternatively, the one or more coating of the one or more polymers on the medical device can include 1) one or more coatings of non-porous polymers; 2) one or more coatings of a combination of one or more porous polymers and one or more non-porous polymers; 3) one or more coating of porous polymer, or 4) one or more combinations of options 1, 2, and 3.

As can be appreciated different agents can be located in and/or between different polymer coating layers and/or on and/or the structure of the medical device. As can also be appreciated, many other and/or additional coating combinations and/or configurations can be used. The concentration of one or more agents, the type of polymer, the type and/or shape of internal structures in the medical device and/or the coating thickness of one or more agents can be used to control the release time, the release rate and/or the dosage amount of one or more agents; however, other or additional combinations can be used. As such, the agent and polymer system combination and location on the medical device can be numerous. As can also be appreciated, one or more agents can be deposited on the top surface of the medical device to provide an initial uncontrolled burst effect of the one or more agents prior to 1) the controlled release of the one or more agents through one or more layers of polymer system that include one or more non-porous polymers and/or 2) the uncontrolled release of the one or more agents through one or more layers of polymer system. The one or more agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition.

The thickness of each polymer layer and/or layer of agent is generally at least about 0.01 µm and is generally less than about 150 µm. In one non-limiting embodiment, the thickness of a polymer layer and/or layer of agent is about 0.02-75 µm, more particularly about 0.05-50 µm, and even more particularly about 1-30 µm.

When the medical device includes and/or is coated with one or more agents such that at least one of the agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely requires reduced use and/or extended use of body-wide therapy after application or insertion of the medical device, or 2) does not require use and/or extended use of body-wide therapy after application or insertion of the medical device. As can be appreciated, use and/or extended use of body-wide therapy can be used after application or insertion of the medical device at the treatment area. In one non-limiting example, no body-wide therapy is needed after the insertion of the medical device into a patient. In another and/or alternative non-limiting example, short-term use of body-wide therapy is needed or used after the insertion of the medical device into a patient. Such short-term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or alternative non-limiting aspect of the present invention, controlled release of one or more agents from the medical device, when controlled release is desired, can be accomplished by using one or more non-porous polymer layers; however, other and/or additional mechanisms can be used to controllably release the one or more agents. The one or more agents are at least partially controllably released by molecular diffusion through the one or more non-porous polymer layers. When one or more non-porous polymer layers are used, the one or more polymer layers are typically biocompatible polymers; however, this is not required. The one or more non-porous polymers can be applied to the medical device without the use of chemicals, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more non-porous polymer layers can be accomplished without increasing the temperature above ambient temperature (e.g., 65-90° F.); however, this is not required. The non-porous polymer system can be mixed with one or more agents prior to being coated on the medical device and/or be coated on a medical device that previously included one or more agents; however, this is not required. The use or one or more non-porous polymer layers allow for accurate controlled release of the agent from the medical device. The controlled release of one or more agents through the non-porous polymer is at least partially controlled on a molecular level utilizing the motility of diffusion of the agent through the non-porous polymer. In one non-limiting example, the one or more non-porous polymer layers can include, but are not limited to, polyamide, parylene (e.g., parylene C, parylene N) and/or a parylene derivative.

In still another and/or alternative non-limiting aspect of the present invention, controlled release of one or more agents from the medical device, when controlled release is desired, can be accomplished by using one or more polymers that form a chemical bond with one or more agents. In one non-limiting example, at least one agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can also be used to control the release rate of one or more agents from the one or more polymers. The amount of agent that can be loaded with one or more polymers may be a function of the concentration of anionic groups and/or cationic groups in the one or more polymer. For agents that are anionic, the concentration of agent that can be loaded on the one or more polymers is generally a function of the concentration of cationic groups (e.g. amine groups and the like) in the one or more polymer and the fraction of these cationic groups that can ionically bind to the anionic form of the one or more agents. For agents that are cationic (e.g., trapidil, etc.), the concentration of agent that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more agents. As such, the concentration of one or more agents that can be bound to the one or more polymers can be varied by controlling the amount of hydrophobic and hydrophilic monomer in the one or more polymers, by controlling the efficiency of salt formation between the agent, and/or the anionic/cationic groups in the one or more polymers.

In still another and/or alternative non-limiting aspect of the present invention, controlled release of one or more agents from the medical device, when controlled release is desired, can be accomplished by using one or more polymers that include one or more induced cross-links. These one or more cross-links can be used to at least partially control the rate of release of the one or more agents from the one or more polymers. The cross-linking in the one or more polymers can be instituted by a number to techniques such as, but not limited to, using catalysts, radiation, heat, and/or the like. The one or more cross-links formed in the one or more polymers can result in the one or more agents becoming partially or fully entrapped within the cross-linking, and/or form a bond with the cross-linking. As such, the partially or fully entrapped agent takes longer to release itself from the cross-linking, thereby delaying the release rate of the one or more agents from the one or more polymers. Consequently, the amount of agent, and/or the rate at which the agent is released from the medical device over time can be at least partially controlled by the amount or degree of cross-linking in the one or more polymers.

In still a further and/or alternative aspect of the present invention, a variety of polymers can be coated on the medical device and/or be used to form at least a portion of the medical device. The one or more polymers can be used on the medical for a variety of reasons such as, but not limited to, 1) forming a portion of the medical device, 2) improving a physical property of the medical device (e.g., improve strength, improve durability, improve biocompatibility, reduce friction, etc.), 3) forming a protective coating on one or more surface structures on the medical device, 4) at least partially forming one or more surface structures on the medical device, and/or 5) at least partially controlling a release rate of one or more agents from the medical device. As can be appreciated, the one or more polymers can have other or additional uses on the medical device. The one or more polymers can be porous, non-porous, biostable, biodegradable (i.e., dissolves, degrades, is absorbed, or any combination thereof in the body), and/or biocompatible. When the medical device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coating of porous polymer, or 5) one or more combinations of options 1, 2, 3 and 4. The thickness of one or more of the polymer layers can be the same or different. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that are considered to be biodegradable, bioresorbable, or bioerodable; polymers that are considered to be biostable; and/or polymers that can be made to be biodegradable and/or bioresorbable with modification. Non-limiting examples of polymers that are considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., nylon 6-6, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); polyvinyl esters (e.g. polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer is generally at least about 0.01 µm and is generally less than about 150 µm; however, other thicknesses can be used. In one non-limiting embodiment, the thickness of a polymer layer and/or layer of agent is about 0.02-75 µm, more particularly about 0.05-50 and even more particularly about 1-30 µm. As can be appreciated, other thicknesses can be used. In one non-limiting embodiment, the medical device includes and/or is coated with parylene, PLGA, POE, PGA, PLLA, PAA, PEG, chitosan and/or derivatives of one or more of these polymers. In another and/or alternative non-limiting embodiment, the medical device includes and/or is coated with a non-porous polymer that includes, but is not limited to, polyamide, Parylene C, Parylene N and/or a parylene derivative. In still another and/or alternative non-limiting embodiment, the medical device includes and/or is coated with poly (ethylene oxide), poly(ethylene glycol), and poly(propylene oxide), polymers of silicone, methane, tetrafluoroethylene (including TEFLON brand polymers), tetramethyldisiloxane, and the like.

In another and/or alternative non-limiting aspect of the present invention, the medical device, when including and/or is coated with one or more agents, can include and/or can be coated with one or more agents that are the same or different in different regions of the medical device and/or have differing amounts and/or concentrations in differing regions of the medical device. For instance, the medical device can 1) be coated with and/or include one or more biologicals on at least one portion of the medical device and at least another portion of the medical device is not coated with and/or includes agent; 2) be coated with and/or include one or more biologicals on at least one portion of the medical device that is different from one or more biologicals on at least another portion of the medical device; 3) be coated with and/or include one or more biologicals at a concentration on at least one portion of the medical device that is different from the concentration of one or more biologicals on at least another portion of the medical device; etc.

In still another and/or alternative non-limiting aspect of the present invention, one or more surfaces of the medical device can be treated to achieve the desired coating properties of the one or more agents and one or more polymers coated on the medical device. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon®, helium, hydrogen, etc. The plasma etching process can be used to clean the surface of the medical device, change the surface properties of the medical device so as to affect the adhesion properties, lubricity properties, etc. of the surface of the medical device. As can be appreciated, other or additional surface treatment processes can be used prior to the coating of one or more agents and/or polymers on the surface of the medical device. In one non-limiting manufacturing process, one or more portions of the medical device are cleaned and/or plasma etched; however, this is not required. Plasma etching can be used to clean the surface of the medical device, and/or to form one or more non-smooth surfaces on the medical device to facilitate in the adhesion of one or more coatings of agents and/or one or more coatings of polymer on the medical device. The gas for the plasma etching can include carbon dioxide and/or other gasses. Once one or more surface regions of the medical device have been treated, one or more coatings of polymer and/or agent can be applied to one or more regions of the medical device. For instance, 1) one or more layers of porous or non-porous polymer can be coated on an outer and/or inner surface of the medical device, 2) one or more layers of agent can be coated on an outer and/or inner surface of the medical device, or 3) one or more layers of porous or non-porous polymer that includes one or more agents can be coated on an outer and/or inner surface of the medical device. The one or more layers of agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of agent and form a mist of very fine droplets. These fine droplets have an average droplet diameter of about 0.1-3 microns. The fine droplet mist facilitates in the formation of a uniform coating thickness and can increase the coverage area on the medical device.

In still yet another and/or alternative non-limiting aspect of the present invention, one or more portions of the medical device can 1) include the same or different agents, 2) include the same or different amount of one or more agents, 3) include the same or different polymer coatings, 4) include the same or different coating thicknesses of one or more polymer coatings, 5) have one or more portions of the medical device controllably release and/or uncontrollably release one or more agents, and/or 6) have one or more portions of the medical device controllably release one or more agents and one or more portions of the medical device uncontrollably release one or more agents.

In yet another and/or alternative non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, inferred waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler-like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal, which at least partially forms the medical device, can function as a marker material; however, this is not required. When the marker material is a flexible material, the marker material typically is formed of one or more polymers that are marker materials in-of-themselves and/or include one or more metal powders and/or metal compounds. In one non-limiting embodiment, the flexible marker material includes one or more metal powders in combinations with parylene, PLGA, POE, PGA, PLLA, PAA, PEG, chitosan and/or derivatives of one or more of these polymers. In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shield the marker material from damage during a medical procedure and/or 4) provide a desired surface profile on the medical device. As can be appreciated, the polymer coating can have other or additional uses. The polymer protective coating can be a biostable polymer or a biodegradable polymer (e.g., degrades and/or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and/or derivatives of one or more of these polymers.

In a further and/or alternative non-limiting aspect of the present invention, the medical device or one or more regions of the medical device can be constructed by use of one or more microelectromechanical manufacturing (MEMS) techniques (e.g., micro-machining, laser micro-machining, laser micro-machining, micro-molding, etc.); however, other or additional manufacturing techniques can be used.

The medical device can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

The medical device can include one or more micro-structures (e.g., micro-needle, micro-pore, micro-cylinder, micro-cone, micro-pyramid, micro-tube, micro-parallelepiped, micro-prism, micro-hemisphere, teeth, rib, ridge, ratchet, hinge, zipper, zip-tie like structure, etc.) on the surface of the medical device. As defined herein, a micro-structure is a structure that has at least one dimension (e.g., average width, average diameter, average height, average length, average depth, etc.) that is no more than about 2 mm, and typically no more than about 1 mm. As can be appreciated, the medical device, when including one or more surface structures, 1) all the surface structures can be micro-structures, 2) all the surface structures can be non-micro-structures, or 3) a portion of the surface structures can be micro-structures and a portion can be non-micro-structures. Non-limiting examples of structures that can be formed on the medical devices are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has be position on and/or in a patient; however, this is not required. The one or more surface structures and/or micro-structures can be used to facilitate in forming maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a agent and/or be formed of a polymer. One or more of the surface structures and/or micro-structures can include one or more internal passageways that can include one or more materials (e.g., agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more agents, adhesives, marker materials and/or polymers to the medical device, 2) changing the appearance or surface characteristics of the medical device, and/or 3) controlling the release rate of one or more agents. The one or more micro-structures and/or surface structures can be biostable, biodegradable, etc. One or more regions of the medical device that are at least partially formed by MEMS techniques can be biostable, biodegradable, etc. The medical device or one or more regions of the medical device can be at least partially covered and/or filled with a protective material so to at least partially protect one or more regions of the medical device, and/or one or more micro-structures and/or surface structures on the medical device from damage.

One or more regions of the medical device, and/or one or more micro-structures and/or surface structures on the medical device can be damaged when the medical device is 1) packaged and/or stored, 2) unpackaged, 3) connected to and/or other secured and/or placed on another medical device, 4) inserted into a treatment area, 5) handled by a user, and/or 6) form a barrier between one or more micro-structures and/or surface structures and fluids in the body passageway. As can be appreciated, the medical device can be damaged in other or additional ways. The protective material can be used to protect the medical device and one or more micro-structures and/or surface structures from such damage. The protective material can include one or more polymers previously identified above. The protective material can be 1) biostable and/or biodegradable and/or 2) porous and/or non-porous.

In one non-limiting design, the polymer is at least partially biodegradable so as to at least partially expose one or more micro-structure and/or surface structure to the environment after the medical device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns, and typically less than about 150 microns; however, other thicknesses can be used. The protective material can be coated by one or more mechanisms previously described herein.

In still yet another and/or alternative non-limiting aspect of the present invention, the medical device can include and/or be used with a physical hindrance. The physical hindrance can include, but is not limited to, an adhesive, sheath, magnet, tape, wire, string, etc. The physical hindrance can be used to 1) physically retain one or more regions of the medical device in a particular form or profile, 2) physically retain the medical device on a particular deployment device, 3) protect one or more surface structures and/or micro-structures on the medical device, and/or 4) form a barrier between one or more surface regions, surface structures and/or micro-structures on the medical device and the fluids in a body passageway. As can be appreciated, the physical hindrance can have other and/or additional functions. The physical hindrance is typically a biodegradable material; however, a biostable material can be used. The physical hindrance can be designed to withstand sterilization of the medical device; however, this is not required. The physical hindrance can be applied to, included in and/or be used in conjunction with one or more medical devices. Additionally or alternatively, the physical hindrance can be designed to be used with and/or conjunction with a medical device for a limited period of time and then 1) disengage from the medical device after the medical device has been partially or fully deployed and/or 2) dissolve and/or degrade during and/or after the medical device has been partially or fully deployed; however, this is not required. Additionally or alternatively, the physical hindrance can be designed and be formulated to be temporarily used with a medical device to facilitate in the deployment of the medical device; however, this is not required. In one non-limiting use of the physical hindrance, the physical hindrance is designed or formulated to at least partially secure a medical device to another device that is used to at least partially transport the medical device to a location for treatment. In another and/or alternative non-limiting use of the physical hindrance, the physical hindrance is designed or formulated to at least partially maintain the medical device in a particular shape or form until the medical device is at least partially positioned in a treatment location. In still another and/or alternative non-limiting use of the physical hindrance, the physical hindrance is designed or formulated to at least partially maintain and/or secure one type of medical device to another type of medical instrument or device until the medical device is at least partially positioned in a treatment location. The physical hindrance can also or alternatively be designed and formulated to be used with a medical device to facilitate in the use of the medical device. In one non-limiting use of the physical hindrance, when in the form of an adhesive, can be formulated to at least partially secure a medical device to a treatment area so as to facilitate in maintaining the medical device at the treatment area. For instance, the physical hindrance can be used in such use to facilitate in maintaining a medical device on or at a treatment area until the medical device is properly secured to the treatment area by sutures, stitches, screws, nails, rod, etc; however, this is not required. Additionally or alternatively, the physical hindrance can be used to facilitate in maintaining a medical device on or at a treatment area until the medical device has partially or fully accomplished its objective. The physical hindrance is typically a biocompatible material so as to not cause unanticipated adverse effects when properly used. The physical hindrance can be biostable or biodegradable (e.g., degrades and/or is absorbed, etc.). When the physical hindrance includes or has one or more adhesives, the one or more adhesives can be applied to the medical device by, but is not limited to, spraying (e.g., atomizing spray techniques, etc.), dip coating, roll coating, sonication, brushing, plasma deposition, and/or depositing by vapor deposition, brushing, painting, etc.) on the medical device. The physical hindrance can also or alternatively form at least a part of the medical device. One or more regions and/or surfaces of a medical device can also or alternatively include the physical hindrance. The physical hindrance can include one or more biological agents and/or other materials (e.g., marker material, polymer, etc.); however, this is not required. When the physical hindrance is or includes an adhesive, the adhesive can be formulated to controllably release one or more biological agents in the adhesive and/or coated on and/or contained within the medical device; however, this is not required. The adhesive can also or alternatively control the release of one or more biological agents located on and/or contained in the medical device by forming a penetrable or non-penetrable bather to such biological agents; however, this is not required. The adhesive can include and/or be mixed with one or more polymers; however, this is not required. The one or more polymers can be used to 1) control the time of adhesion provided by said adhesive, 2) control the rate of degradation of the adhesive, and/or 3) control the rate of release of one or more biological agents from the adhesive and/or diffusing or penetrating through the adhesive layer; however, this is not required. When the physical hindrance includes a sheath, the sheath can be designed to partially or fully encircle the medical device. The sheath can be designed to be physically removed from the medical device after the medical device is deployed to a treatment area; however, this is not required. The sheath can be formed of a biodegradable material that at least partially degrades over time to at least partially expose one or more surface regions, micro-structures and/or surface structures of the medical device; however, this is not required. The sheath can include and/or be at least partially coated with one or more biological agents. The sheath includes one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more biological agents from the sheath. As can be appreciated, the one or more polymers can have other or additional uses on the sheath.

In another and/or alternative non-limiting aspect of the invention, the medical device can include a bistable construction. In such a design, the medical device has two or more stable configurations, including a first stable configuration with a first cross-sectional shape and a second stable configuration with a second cross-sectional shape. All or a portion of the medical device can include the bistable construction. The bistable construction can result in a generally uniform change in shape of the medical device, or one portion of the medical device can change into one or more configurations and one or more other portions of the medical device can change into one or more other configurations.

In still another and/or alternative aspect of the invention, the medical device can be an expandable device that can be expanded by use of some other device (e.g., balloon, etc.) and/or is self-expanding. The expandable medical device can be fabricated from a material that has no or substantially no shape-memory characteristics or can be partially fabricated from a material having shape-memory characteristics. Typically, when one or more shape-memory materials are used, the shape-memory material composition is selected such that the shape-memory material remains in an unexpanded configuration at a cold temperature (e.g., below body temperature); however, this is not required. When the shape-memory material is heated (e.g., to body temperature) the expandable body section can be designed to expand to at least partially seal and secure the medical device in a body passageway or other region; however, this is not required.

In still another and/or alternative non-limiting aspect of the invention, the medical device can be used in conjunction with one or more other biological agents that are not on the medical device. For instance, the success of the medical device can be improved by infusing, injecting or consuming orally one or more biological agents. Such biological agents can be the same and/or different from the one or more biological agents on and/or in the medical device. Such use of one or more biological agents are commonly used in systemic treatment of a patient after a medical procedure, such as body-wide therapy, after the medical device has been inserted in the treatment area can be reduced or eliminated by use of the novel alloy. Although the medical device of the present invention can be designed to reduce or eliminate the need for long periods of body-wide therapy after the medical device has been inserted in the treatment area, the use of one or more biological agents can be used in conjunction with the medical device to enhance the success of the medical device and/or reduce or prevent the occurrence of one or more biological problems (e.g., infection, rejection of the medical device, etc.). For instance, solid dosage forms of biological agents for oral administration, and/or for other types of administration (e.g., suppositories, etc.) can be used. Such solid forms can include, but are not limited to, capsules, tablets, effervescent tablets, chewable tablets, pills, powders, sachets, granules and gels. The solid form of the capsules, tablets, effervescent tablets, chewable tablets, pills, etc. can have a variety of shapes such as, but not limited to, spherical, cubical, cylindrical, pyramidal, and the like. In such solid dosage form, one or more biological agents can be admixed with at least one filler material such as, but not limited to, sucrose, lactose or starch; however, this is not required. Such dosage forms can include additional substances such as, but not limited to, inert diluents (e.g., lubricating agents, etc.). When capsules, tablets, effervescent tablets or pills are used, the dosage form can also include buffering agents; however, this is not required. Soft gelatin capsules can be prepared to contain a mixture of the one or more biological agents in combination with vegetable oil or other types of oil; however, this is not required. Hard gelatin capsules can contain granules of the one or more biological agents in combination with a solid carrier such as, but not limited to, lactose, potato starch, corn starch, cellulose derivatives of gelatin, etc.; however, this is not required. Tablets and pills can be prepared with enteric coatings for additional time release characteristics; however, this is not required. Liquid dosage forms of the one or more biological agents for oral administration can include pharmaceutically acceptable emulsions, solutions, suspensions, syrups, elixirs, etc.; however, this is not required. In one non-limiting embodiment, when at least a portion of one or more biological agents is inserted into a treatment area (e.g., gel form, paste form, etc.) and/or provided orally (e.g., pill, capsule, etc.) and/or anally (suppository, etc.), one or more of the biological agents can be controllably released; however, this is not required. In one non-limiting example, one or more biological agents can be given to a patient in solid dosage form and one or more of such biological agents can be controllably released from such solid dosage forms. In another and/or alternative non-limiting example trapidil, trapidil derivatives, taxol, taxol derivatives, cytochalasin, cytochalasin derivatives, paclitaxel, paclitaxel derivatives, rapamycin, rapamycin derivatives, 5-phenylmethimazole, 5-phenylmethimazole derivatives, GM-CSF, GM-CSF derivatives, or combinations thereof are given to a patient prior to, during and/or after the insertion of the medical device in a treatment area. As can be appreciated, other or additional biological agents can be used.

Certain types of biological agents may be desirable to be present in a treated area for an extended period of time in order to utilize the full or nearly full clinical potential of the biological agent. For instance, trapidil and/or trapidil derivatives is a compound that has many clinical attributes including, but not limited to, anti-platelet effects, inhibition of smooth muscle cells and monocytes, fibroblast proliferation and increased MAPK-1 which in turn deactivates kinase, a vasodilator, etc. These attributes can be effective in improving the success of a medical device that has been inserted at a treatment area. In some situations, these positive effects of trapidil and/or trapidil derivatives need to be prolonged in a treatment area in order to achieve complete clinical competency. Trapidil and/or trapidil derivatives have a half life in vivo of about 2-4 hours with hepatic clearance of 48 hours. In order to utilize the full clinical potential of trapidil and/or trapidil derivatives, trapidil and/or trapidil derivatives should be metabolized over an extended period of time without interruption; however, this is not required. By inserting trapidil and/or trapidil derivatives in a solid dosage form, the trapidil and/or trapidil derivatives could be released in a patient over extended periods of time in a controlled manner to achieve complete or nearly complete clinical competency of the trapidil and/or trapidil derivatives.

In another and/or alternative non-limiting example, one or more biological agents are at least partially encapsulated in one or more polymers. The one or more polymers can be biodegradable, non-biodegradable, porous, and/or non-porous. When the one or more polymers are biodegradable, the rate of degradation of the one or more biodegradable polymers can be used to at least partially control the rate at which one or more biological agents are released into a body passageway and/or other parts of the body over time. The one or more biological agents can be at least partially encapsulated with different polymer coating thickness, different numbers of coating layers, and/or with different polymers to alter the rate at which one or more biological agents are released in a body passageway and/or other parts of the body over time. The rate of degradation of the polymer is principally a function of the 1) water permeability and solubility of the polymer, 2) chemical composition of the polymer and/or biological agent, 3) mechanism of hydrolysis of the polymer, 4) biological agent encapsulated in the polymer, 5) size, shape and surface volume of the polymer, 6) porosity of the polymer, 7) molecular weight of the polymer, 8) degree of cross-linking in the polymer, 9) degree of chemical bonding between the polymer and biological agent, and/or 10) structure of the polymer and/or biological agent. As can be appreciated, other factors may also affect the rate of degradation of the polymer. When the one or more polymers are biostable, the rate at when the one or more biological agents are released from the biostable polymer is a function of the 1) porosity of the polymer, 2) molecular diffusion rate of the biological agent through the polymer, 3) degree of cross-linking in the polymer, 4) degree of chemical bonding between the polymer and biological agent, 5) chemical composition of the polymer and/or biological agent, 6) biological agent encapsulated in the polymer, 7) size, shape and surface volume of the polymer, and/or 8) structure of the polymer and/or biological agent. As can be appreciated, other factors may also affect the rate of release of the one or more biological agents from the biostable polymer. Many different polymers can be used such as, but not limited to, aliphatic polyester compounds (e.g., PLA (i.e., poly (D, L-lactic acid), poly (L-lactic acid)), PLGA (i.e. poly (lactide-co-glycoside), etc.), POE, PEG, PLLA, parylene, chitosan and/or derivatives thereof. As can be appreciated, the at least partially encapsulated biological agent can be introduced into a patient by means other than by oral introduction, such as, but not limited to, injection, topical applications, intravenously, eye drops, nasal spray, surgical insertion, suppositories, intrarticularly, intraocularly, intranasally, intradermally, sublingually, intravesically, intrathecally, intraperitoneally, intracranially, intramuscularly, subcutaneously, directly at a particular site, and the like.

In a further and/or alternative non-limiting aspect of the present invention, the novel alloy used to at least partially form the medical device is initially formed into a blank, a rod, a tube, etc. and then finished into final form by one or more finishing processes. The metal alloy blank, rod, tube, etc. can be formed by various techniques such as, but not limited to, 1) melting the metal alloy and/or metals that form the metal alloy (e.g., vacuum arc melting, etc.) and then extruding and/or casting the metal alloy into a blank, rod, tube, etc., 2) melting the metal alloy and/or metals that form the metal alloy, forming a metal strip and then rolling and welding the strip into a blank, rod, tube, etc., or 3) consolidating metal powder of the metal alloy and/or metal powder of metals that form the metal alloy into a blank, rod, tube, etc. When the metal alloy is formed into a blank, the shape and size of the blank is non-limiting. When the metal alloy is formed into a rod or tube, the rod or tube generally has a length of about 48 inches or less; however, longer lengths can be formed. In one non-limiting arrangement, the length of the rod or tube is about 8-20 inches. The average outer diameter of the rod or tube is generally less than about 2 inches (i.e., less than about 3.14 sq. in. cross-sectional area), more typically less than about 1 inch outer diameter, and even more typically no more than about 0.5 inch outer diameter; however, larger rod or tube diameter sizes can be formed. In one non-limiting configuration for a tube, the tube has an inner diameter of about 0.31 inch plus or minus about 0.002 inch and an outer diameter of about 0.5 inch plus or minus about 0.002 inch. The wall thickness of the tube is about 0.095 inch plus or minus about 0.002 inch. As can be appreciated, this is just one example of many different sized tubes that can be formed. In one non-limiting process, the blank, rod, tube, etc. can be formed from one or more ingots of metal or metal alloy. In one non-limiting process, an arc melting process (e.g., vacuum arc melting process, etc.) can be used to form the blank, rod, tube, etc. In another non-limiting process, rhenium powder and molybdenum powder, tungsten and tantalum powder, cobalt and chromium powder can be placed in a crucible (e.g., silica crucible, etc.) and heated under a controlled atmosphere (e.g., vacuum environment, carbon monoxide environment, hydrogen and argon environment, helium, argon, etc.) by an induction melting furnace to form the blank, rod, tube, etc. As can be appreciated, other metal particles can be used to form other metal alloys. It can be appreciated that other or additional processes can be used to form the blank, rod, tube, etc. When a tube of metal alloy is to be formed, a close-fitting rod can be used during the extrusion process to form the tube; however, this is not required. In another and/or additional non-limiting process, the tube of the metal alloy can be formed from a strip or sheet of metal alloy. The strip or sheet of metal alloy can be formed into a tube by rolling the edges of the sheet or strip and then welding together the edges of the sheet or strip. The welding of the edges of the sheet or strip can be accomplished in several ways such as, but not limited to, a) holding the edges together and then e-beam welding the edges together in a vacuum, b) positioning a thin strip of metal alloy above and/or below the edges of the rolled strip or sheet to be welded, then welding the one or more strips along the rolled strip or sheet edges, and then grinding off the outer strip, or c) laser welding the edges of the rolled sheet or strip in a vacuum, oxygen reducing atmosphere, or inert atmosphere. In still another and/or additional non-limiting process, the blank, rod, tube, etc. of the metal alloy is formed by consolidating metal powder. In this process, fine particles of molybdenum and rhenium, tungsten and tantalum, cobalt chromium along with any additives are mixed to form a homogenous blend of particles. As can be appreciated, other metal particles can be used to form other metal alloys. Typically, the average particle size of the metal powders is less than about 200 mesh (e.g., less than 74 microns). A larger average particle size can interfere with the proper mixing of the metal powders and/or adversely affect one or more physical properties of the blank, rod, tube, etc. formed from the metal powders. In one non-limiting embodiment, the average particle size of the metal powders is less than about 230 mesh (e.g., less than 63 microns). In another and/or alternative non-limiting embodiment, the average particle size of the metal powders is about 2-63 microns, and more particularly about 5-40 microns. As can be appreciated, smaller average particle sizes can be used. The purity of the metal powders should be selected so that the metal powders contain very low levels of carbon, oxygen and nitrogen. Typically, the carbon content of the molybdenum metal powder is less than about 100 ppm, the oxygen content of the molybdenum metal powder is less than about 50 ppm, and the nitrogen content of the molybdenum metal powder is less than about 20 ppm. Typically, the carbon content of the rhenium metal powder is less than about 100 ppm, the oxygen content of the rhenium metal powder is less than about 50 ppm, and the nitrogen content of the rhenium metal powder is less than about 20 ppm. Typically, metal powder having a purity grade of at least 99.9 and more typically at least about 99.95 should be used to obtain the desired purity of the powders of molybdenum and rhenium. Similar purities are desirable for the tungsten and tantalum when forming the tungsten and tantalum alloy, or for cobalt and chromium when forming the cobalt-chromium alloy. When titanium, yttrium, zirconium, and/or some or metal additive powder is added to the metal powder mixture, the amount of carbon, oxygen and nitrogen in the powder should generally be minimized Typically, metal powder having a purity grade of at least 99.8 and more typically at least about 99.9 should be used to obtain the desired purity of the powders of any metal additive. The blend of metal powder is then pressed together to form a solid solution of the metal alloy into blank, rod, tube, etc. Typically the pressing process is by an isostatic process (i.e., uniform pressure applied from all sides on the metal powder); however other processes can be used. When the metal powders are pressed together isostatically, cold isostatic pressing (CIP) is typically used to consolidate the metal powders; however, this is not required. The pressing process can be performed in an inert atmosphere, an oxygen reducing atmosphere (e.g., hydrogen, argon and hydrogen mixture, etc.) and/or under a vacuum; however, this is not required. The average density of the blank, rod, tube, etc. that is achieved by pressing together the metal powders is about 80-90% of the final average density of the blank, rod, tube, etc. or about 70-96% the minimum theoretical density of the metal alloy. Pressing pressures of at least about 300 MPa are generally used. Generally, the pressing pressure is about 400-700 MPa; however, other pressures can be used. After the metal powders are pressed together, the pressed metal powders are sintered at high temperature (e.g., 2000-3000° C.) to fuse the metal powders together to form the blank, rod, tube, etc. The sintering of the consolidated metal powder can be performed in an oxygen reducing atmosphere (e.g., helium, argon, hydrogen, argon and hydrogen mixture, etc.) and/or under a vacuum; however, this is not required. At the high sintering temperatures, a high hydrogen atmosphere will reduce both the amount of carbon and oxygen in the formed blank, rod, tube, etc. The sintered metal powder generally has an as-sintered average density of about 90-99% the minimum theoretical density of the metal alloy. Typically, the sintered blank, rod, tube, etc. has a final average density of at least about 8 gm/cc, and typically at least about 8.3 gm/cc, and can be up to or greater than about 16 gm/cc. The density of the formed blank, rod, tube, etc. will generally depend on the type of metal alloy sued to form the blank, rod, tube, etc.

In still a further and/or alternative non-limiting aspect of the present invention, when a solid rod of the metal alloy is formed, the rod is then formed into a tube prior to reducing the outer cross-sectional area or diameter of the rod. The rod can be formed into a tube by a variety of processes such as, but not limited to, cutting or drilling (e.g., gun drilling, etc.) or by cutting (e.g., EDM, etc.). The cavity or passageway formed in the rod typically is formed fully through the rod; however, this is not required.

In yet a further and/or alternative non-limiting aspect of the present invention, the blank, rod, tube, etc. can be cleaned and/or polished after the blank, rod, tube, etc. has been formed; however, this is not required. Typically, the blank, rod, tube, etc. is cleaned and/or polished prior to being further processed; however, this is not required. When a rod of the metal alloy is formed into a tube, the formed tube is typically cleaned and/or polished prior to being further processed; however, this is not required. When the blank, rod, tube, etc. is resized and/or annealed, the resized and/or annealed blank, rod, tube, etc. is typically cleaned and/or polished prior to and/or after each or after a series of resizing and/or annealing processes; however, this is not required. The cleaning and/or polishing of the blank, rod, tube, etc. is used to remove impurities and/or contaminants from the surfaces of the blank, rod, tube, etc. Impurities and contaminants can become incorporated into the metal alloy during the processing of the blank, rod, tube, etc. The inadvertent incorporation of impurities and contaminants in the blank, rod, tube, etc. can result in an undesired amount of carbon, nitrogen and/or oxygen, and/or other impurities in the metal alloy. The inclusion of impurities and contaminants in the metal alloy can result in premature micro-cracking of the metal alloy and/or an adverse effect on one or more physical properties of the metal alloy (e.g., decrease in tensile elongation, increased ductility, increased brittleness, etc.). The cleaning of the metal alloy can be accomplished by a variety of techniques such as, but not limited to, 1) using a solvent (e.g., acetone, methyl alcohol, etc.) and wiping the metal alloy with a Kimwipe or other appropriate towel, 2) by at least partially dipping or immersing the metal alloy in a solvent and then ultrasonically cleaning the metal alloy, and/or 3) by at least partially dipping or immersing the metal alloy in a pickling solution. As can be appreciated, the metal alloy can be cleaned in other or additional ways. If the metal alloy is to be polished, the metal alloy is generally polished by use of a polishing solution that typically includes an acid solution; however, this is not required. In one non-limiting example, the polishing solution includes sulfuric acid; however, other or additional acids can be used. In one non-limiting polishing solution, the polishing solution can include by volume 60-95% sulfuric acid and 5-40% de-ionized water (DI water). Typically, the polishing solution that includes an acid will increase in temperature during the making of the solution and/or during the polishing procedure. As such, the polishing solution is typically stirred and/or cooled during making of the solution and/or during the polishing procedure. The temperature of the polishing solution is typically about 20-100° C., and typically greater than about 25° C. One non-limiting polishing technique that can be used is an electro-polishing technique. When an electro-polishing technique is used, a voltage of about 2-30V, and typically about 5-12V is applied to the blank, rod, tube, etc. during the polishing process; however, it will be appreciated that other voltages can be used. The time used to polish the metal alloy is dependent on both the size of the blank, rod, tube, etc. and the amount of material that needs to be removed from the blank, rod, tube, etc. The blank, rod, tube, etc. can be processed by use of a two-step polishing process wherein the metal alloy piece is at least partially immersed in the polishing solution for a given period (e.g., 0.1-15 minutes, etc.), rinsed (e.g., DI water, etc.) for a short period of time (e.g., 0.02-1 minute, etc.), and then flipped over and at least partially immersed in the solution again for the same or similar duration as the first time; however, this is not required. The metal alloy can be rinsed (e.g., DI water, etc.) for a period of time (e.g., 0.01-5 minutes, etc.) before rinsing with a solvent (e.g., acetone, methyl alcohol, etc.); however, this is not required. The metal alloy can be dried (e.g., exposure to the atmosphere, maintained in an inert gas environment, etc.) on a clean surface. These polishing procedures can be repeated until the desired amount of polishing of the blank, rod, tube, etc. is achieved. The blank, rod, tube, etc. can be uniformly electro-polished or selectively electro-polished. When the blank, rod, tube, etc. is selectively electro-polished, the selective electro-polishing can be used to obtain different surface characteristics of the blank, rod, tube, etc. and/or selectively expose one or more regions of the blank, rod, tube, etc.; however, this is not required.

In still yet a further and/or alternative non-limiting aspect of the present invention, the blank, rod, tube, etc. can be resized to the desired dimension of the medical device. In one non-limiting embodiment, the cross-sectional area or diameter of the blank, rod, tube, etc. is reduced to a final blank, rod, tube, etc. dimension in a single step or by a series of steps. The reduction of the outer cross-sectional area or diameter of the blank, rod, tube, etc. may be obtained by centerless grinding, turning, electro-polishing, drawing process, grinding, laser cutting, shaving, polishing, EDM cutting, etc. The outer cross-sectional area or diameter size of the blank, rod, tube, etc. can be reduced by the use of one or more drawing processes; however, this is not required. During the drawing process, care should be taken to not form micro-cracks in the blank, rod, tube, etc. during the reduction of the blank, rod, tube, etc. outer cross-sectional area or diameter. Generally, the blank, rod, tube, etc. should not be reduced in cross-sectional area by more about 25% each time the blank, rod, tube, etc. is drawn through a reducing mechanism (e.g., a die, etc.). In one non-limiting process step, the blank, rod, tube, etc. is reduced in cross-sectional area by about 0.1-20% each time the blank, rod, tube, etc. is drawn through a reducing mechanism. In another and/or alternative non-limiting process step, the blank, rod, tube, etc. is reduced in cross-sectional area by about 1-15% each time the blank, rod, tube, etc. is drawn through a reducing mechanism. In still another and/or alternative non-limiting process step, the blank, rod, tube, etc. is reduced in cross-sectional area by about 2-15% each time the blank, rod, tube, etc. is drawn through reducing mechanism. In yet another one non-limiting process step, the blank, rod, tube, etc. is reduced in cross-sectional area by about 5-10% each time the blank, rod, tube, etc. is drawn through reducing mechanism. In another and/or alternative non-limiting embodiment of the invention, the blank, rod, tube, etc. of metal alloy is drawn through a die to reduce the cross-sectional area of the blank, rod, tube, etc. Generally, before drawing the blank, rod, tube, etc. through a die, one end of the blank, rod, tube, etc. is narrowed down (nosed) so as to allow it to be fed through the die; however, this is not required. The tube drawing process is typically a cold drawing process or a plug drawing process through a die. When a cold drawing or mandrel drawing process is used, a lubricant (e.g., molybdenum paste, grease, etc.) is typically coated on the outer surface of the blank, rod, tube, etc. and the blank, rod, tube, etc. is then drawn though the die. Typically, little or no heat is used during the cold drawing process. After the blank, rod, tube, etc. has been drawn through the die, the outer surface of the blank, rod, tube, etc. is typically cleaned with a solvent to remove the lubricant so as to limit the amount of impurities that are incorporated in the metal alloy; however, this is not required. This cold drawing process can be repeated several times until the desired outer cross-sectional area or diameter, inner cross-sectional area or diameter and/or wall thickness of the blank, rod, tube, etc. is achieved. A plug drawing process can also or alternatively be used to size the blank, rod, tube, etc. The plug drawing process typically does not use a lubricant during the drawing process. The plug drawing process typically includes a heating step to heat the blank, rod, tube, etc. prior and/or during the drawing of the blank, rod, tube, etc. through the die. The elimination of the use of a lubricant can reduce the incidence of impurities being introduced into the metal alloy during the drawing process. During the plug drawing process, the blank, rod, tube, etc. can be protected from oxygen by use of a vacuum environment, a non-oxygen environment (e.g., hydrogen, argon and hydrogen mixture, nitrogen, nitrogen and hydrogen, etc.) or an inert environment. One non-limiting protective environment includes argon, hydrogen or argon and hydrogen; however, other or additional inert gasses can be used. As indicated above, the blank, rod, tube, etc. is typically cleaned after each drawing process to remove impurities and/or other undesired materials from the surface of the blank, rod, tube, etc.; however, this is not required. Typically, the blank, rod, tube, etc. should be shielded from oxygen and nitrogen when the temperature of the blank, rod, tube, etc. is increased to above 500° C., and typically above 450° C., and more typically above 400° C.; however, this is not required. When the blank, rod, tube, etc. is heated to temperatures above about 400-500° C., the blank, rod, tube, etc. has a tendency to begin form nitrides and/or oxides in the presence of nitrogen and oxygen. In these higher temperature environments, a hydrogen environment, argon and hydrogen environment, etc. is generally used. When the blank, rod, tube, etc. is drawn at temperatures below 400-500° C., the blank, rod, tube, etc. can be exposed to air with little or no adverse effects; however, an inert or slightly reducing environment is generally more desirable.

In still a further and/or alternative non-limiting aspect of the present invention, the blank, rod, tube, etc. during the drawing process can be nitrided; however, this is not required. The nitride layer on the blank, rod, tube, etc. can function as a lubricating surface during the drawing process to facilitate in the drawing of the blank, rod, tube, etc. The blank, rod, tube, etc. is generally nitrided in the presence of nitrogen or a nitrogen mixture (e.g., 97% N-3% H, etc.) for at least about 1 minute at a temperature of at least about 400° C. In one-limiting nitriding process, the blank, rod, tube, etc. is heated in the presence of nitrogen or a nitrogen-hydrogen mixture to a temperature of about 400-800° C. for about 1-30 minutes. In one non-limiting embodiment of the invention, the surface of the blank, rod, tube, etc. is nitrided prior to at least one drawing step for the blank, rod, tube, etc. In one non-limiting aspect of this embodiment, the surface of the blank, rod, tube, etc. is nitrided prior to a plurality of drawing steps. In another non-limiting aspect of this invention, after the blank, rod, tube, etc. has been annealed, the blank, rod, tube, etc. is nitrided prior to being drawn. In another and/or alternative non-limiting embodiment, the blank, rod, tube, etc. is cleaned to remove nitride compounds on the surface of the blank, rod, tube, etc. prior to annealing the rod to tube. The nitride compounds can be removed by a variety of steps such as, but not limited to, and grit blasting, polishing, etc. After the blank, rod, tube, etc. has been annealed, the blank, rod, tube, etc. can be again nitrided prior to one or more drawing steps; however, this is not required. As can be appreciated, the complete outer surface of the blank, rod, tube, etc. can be nitrided or a portion of the outer surface of the blank, rod, tube, etc. can be nitrided. Nitriding only selected portions of the outer surface of the blank, rod, tube, etc. can be used to obtain different surface characteristics of the blank, rod, tube, etc.; however, this is not required.

In yet a further and/or alternative non-limiting aspect of the present invention, the blank, rod, tube, etc. is cooled after being annealed; however, this is not required. Generally, the blank, rod, tube, etc. is cooled at a fairly quickly rate after being annealed so as to inhibit or prevent the formation of a sigma phase in the metal alloy; however, this is not required. Generally, the blank, rod, tube, etc. is cooled at a rate of at least about 50° C. per minute after being annealed, typically at least about 100° C. per minute after being annealed, more typically about 75-500° C. per minute after being annealed, even more typically about 100-400° C. per minute after being annealed, still even more typically about 150-350° C. per minute after being annealed, and yet still more typically about 200-300° C. per minute after being annealed, and still yet even more typically about 250-280° C. per minute after being annealed; however, this is not required.

In still yet a further and/or alternative non-limiting aspect of the present invention, the blank, rod, tube, etc. is annealed after one or more drawing processes. The metal alloy blank, rod, tube, etc. can be annealed after each drawing process or after a plurality of drawing processes. The metal alloy blank, rod, tube, etc. is typically annealed prior to about a 60% cross-sectional area size reduction of the metal alloy blank, rod, tube, etc. In other words, the blank, rod, tube, etc. should not be reduced in cross-sectional area by more than 60% before being annealed. A too large of a reduction in the cross-sectional area of the metal alloy blank, rod, tube, etc. during the drawing process prior to the blank, rod, tube, etc. being annealed can result in micro-cracking of the blank, rod, tube, etc. In one non-limiting processing step, the metal alloy blank, rod, tube, etc. is annealed prior to about a 50% cross-sectional area size reduction of the metal alloy blank, rod, tube, etc. In another and/or alternative non-limiting processing step, the metal alloy blank, rod, tube, etc. is annealed prior to about a 45% cross-sectional area size reduction of the metal alloy blank, rod, tube, etc. In still another and/or alternative non-limiting processing step, the metal alloy blank, rod, tube, etc. is annealed prior to about a 1-45% cross-sectional area size reduction of the metal alloy blank, rod, tube, etc. In yet another and/or alternative non-limiting processing step, the metal alloy blank, rod, tube, etc. is annealed prior to about a 5-30% cross-sectional area size reduction of the metal alloy blank, rod, tube, etc. In still yet another and/or alternative non-limiting processing step, the metal alloy blank, rod, tube, etc. is annealed prior to about a 5-15% cross-sectional area size reduction of the metal alloy blank, rod, tube, etc. When the blank, rod, tube, etc. is annealed, the blank, rod, tube, etc. is typically heated to a temperature of about 800-1700° C. for a period of about 2-200 minutes; however, other temperatures and/or times can be used. In one non-limiting processing step, the metal alloy blank, rod, tube, etc. is annealed at a temperature of about 1000-1600° C. for about 2-100 minutes. In another non-limiting processing step, the metal alloy blank, rod, tube, etc. is annealed at a temperature of about 1100-1500° C. for about 5-30 minutes. The annealing process typically occurs in an inert environment or an oxygen reducing environment so as to limit the amount of impurities that may embed themselves in the metal alloy during the annealing process. One non-limiting oxygen reducing environment that can be used during the annealing process is a hydrogen environment; however, it can be appreciated that a vacuum environment can be used or one or more other or additional gasses can be used to create the oxygen reducing environment. At the annealing temperatures, a hydrogen containing atmosphere can further reduce the amount of oxygen in the blank, rod, tube, etc. The chamber in which the blank, rod, tube, etc. is annealed should be substantially free of impurities (e.g., carbon, oxygen, and/or nitrogen) so as to limit the amount of impurities that can embed themselves in the blank, rod, tube, etc. during the annealing process. The annealing chamber typically is formed of a material that will not impart impurities to the blank, rod, tube, etc. as the blank, rod, tube, etc. is being annealed. A non-limiting material that can be used to form the annealing chamber includes, but is not limited to, molybdenum, rhenium, tungsten, molybdenum TZM alloy, cobalt, chromium, ceramic, etc. When the blank, rod, tube, etc. is restrained in the annealing chamber, the restraining apparatuses that are used to contact the metal alloy blank, rod, tube, etc. are typically formed of materials that will not introduce impurities to the metal alloy during the processing of the blank, rod, tube, etc. Non-limiting examples of materials that can be used to at least partially form the restraining apparatuses include, but are not limited to, molybdenum, titanium, yttrium, zirconium, rhenium, cobalt, chromium, tantalum, and/or tungsten. In still another and/or alternative non-limiting processing step, the parameters for annealing can be changed as the blank, rod, tube, etc. as the cross-sectional area or diameter; and/or wall thickness of the blank, rod, tube, etc. are changed. It has been found that good grain size characteristics of the tube can be achieved when the annealing parameters are varied as the parameters of the blank, rod, tube, etc. change. For example, as the wall thickness is reduced, the annealing temperature is correspondingly reduced; however, the times for annealing can be increased. As can be appreciated, the annealing temperatures of the blank, rod, tube, etc. can be decreased as the wall thickness decreases, but the annealing times can remain the same or also be reduced as the wall thickness reduces. After each annealing process, the grain size of the metal in the blank, rod, tube, etc. should be no greater than 4 ASTM. Generally the grain size range is about 4-14 ASTM. Grain sizes of 7-14 ASTM can be achieved by the annealing process of the present invention. It is believed that as the annealing temperature is reduced as the wall thickness reduces, small grain sizes can be obtained. The grain size of the metal in the blank, rod, tube, etc. should be as uniform as possible. In addition, the sigma phase of the metal in the blank, rod, tube, etc. should be as reduced as much as possible. The sigma phase is a spherical, elliptical or tetragonal crystalline shape in the metal alloy. The sigma phase is commonly formed of both rhenium and molybdenum, typically with a larger concentration of rhenium. After the final drawing of the blank, rod, tube, etc., a final annealing of the blank, rod, tube, etc. can be done for final strengthening of the blank, rod, tube, etc.; however, this is not required. This final annealing process, when used, generally occurs at a temperature of about 900-1600° C. for at least about 5 minutes; however, other temperatures and/or time periods can be used.

In another and/or alternative non-limiting aspect of the present invention, the blank, rod, tube, etc. can be cleaned prior to and/or after being annealed. The cleaning process is designed to remove impurities, lubricants (e.g., nitride compounds, molybdenum paste, grease, etc.) and/or other materials from the surfaces of the blank, rod, tube, etc. Impurities that are on one or more surfaces of the blank, rod, tube, etc. can become permanently embedded into the blank, rod, tube, etc. during the annealing processes. These imbedded impurities can adversely affect the physical properties of the metal alloy as the blank, rod, tube, etc. is formed into a medical device, and/or can adversely affect the operation and/or life of the medical device. In one non-limiting embodiment of the invention, the cleaning process includes a delubrication or degreasing process which is typically followed by pickling process; however, this is not required. The delubrication or degreasing process followed by pickling process are typically used when a lubricant has been used on the blank, rod, tube, etc. during a drawing process. Lubricants commonly include carbon compounds, nitride compounds, molybdenum paste, and other types of compounds that can adversely affect the metal alloy if such compounds and/or elements in such compounds become associated and/or embedded with the metal alloy during an annealing process. The delubrication or degreasing process can be accomplished by a variety of techniques such as, but not limited to, 1) using a solvent (e.g., acetone, methyl alcohol, etc.) and wiping the metal alloy with a Kimwipe or other appropriate towel, 2) by at least partially dipping or immersing the metal alloy in a solvent and then ultrasonically cleaning the metal alloy, 3) sand blasting the metal alloy, and/or 4) chemical etching the metal alloy. As can be appreciated, the metal alloy can be delubricated or degreased in other or additional ways. After the metal alloy blank, rod, tube, etc. has been delubricated or degreased, the blank, rod, tube, etc. can be further cleaned by use of a pickling process; however, this is not required. The pickling process, when used, includes the use of one or more acids to remove impurities from the surface of the blank, rod, tube, etc. Non-limiting examples of acids that can be used as the pickling solution include, but are not limited to, nitric acid, acetic acid, sulfuric acid, hydrochloric acid, and/or hydrofluoric acid. These acids are typically analytical reagent (ACS) grade acids. The acid solution and acid concentration are selected to remove oxides and other impurities on the blank, rod, tube, etc. surface without damaging or over etching the surface of the blank, rod, tube, etc. A blank, rod, tube, etc. surface that includes a large amount of oxides and/or nitrides typically requires a stronger pickling solution and/or long picking process times. Non-limiting examples of pickling solutions include 1) 25-60% DI water, 30-60% nitric acid, and 2-20% sulfuric acid; 2) 40-75% acetic acid, 10-35% nitric acid, and 1-12% hydrofluoric acid; and 3) 50-100% hydrochloric acid. As can be appreciated, one or more different pickling solutions can be used during the pickling process. During the pickling process, the blank, rod, tube, etc. is fully or partially immersed in the pickling solution for a sufficient amount of time to remove the impurities from the surface of the blank, rod, tube, etc. Typically, the time period for pickling is about 2-120 seconds; however, other time periods can be used. After the blank, rod, tube, etc. has been pickled, the blank, rod, tube, etc. is typically rinsed with a water (e.g., DI water, etc.) and/or a solvent (e.g., acetone, methyl alcohol, etc.) to remove any pickling solution from the blank, rod, tube, etc. and then the blank, rod, tube, etc. is allowed to dry. The blank, rod, tube, etc. may be keep in a protective environment during the rinse and/or drying process to inhibit or prevent oxides from reforming on the surface of the blank, rod, tube, etc. prior to the blank, rod, tube, etc. being drawn and/or annealed; however, this is not required.

In yet another and/or alternative non-limiting aspect of the present invention, the restraining apparatuses that are used to contact the metal alloy blank, rod, tube, etc. during an annealing process and/or drawing process are typically formed of materials that will not introduce impurities to the metal alloy during the processing of the blank, rod, tube, etc. In one non-limiting embodiment, when the metal alloy blank, rod, tube, etc. is exposed to temperatures above 150° C., the materials that contact the metal alloy blank, rod, tube, etc. during the processing of the blank, rod, tube, etc. are typically made from chromium, cobalt, molybdenum, rhenium, tantalum and/or tungsten. When the metal alloy blank, rod, tube, etc. is processed at lower temperatures (i.e., 150° C. or less), materials made from Teflon parts can also or alternatively be used.

In still another and/or alternative non-limiting aspect of the present invention, the metal alloy blank, rod, tube, etc., after being formed to the desired shape, outer cross-sectional area or diameter, inner cross-sectional area or diameter and/or wall thickness, can be cut and/or etched to at least partially form the desired configuration of the medical device (e.g., stent, pedicle screw, PFO device, valve, spinal implant, vascular implant, graft, guide wire, sheath, stent catheter, electrophysiology catheter, hypotube, catheter, staple, cutting device, dental implant, bone implant, prosthetic implant or device to repair, replace and/or support a bone and/or cartilage, nail, rod, screw, post, cage, plate, cap, hinge, joint system, wire, anchor, spacer, shaft, anchor, disk, ball, tension band, locking connector, or other structural assembly that is used in a body to support a structure, mount a structure and/or repair a structure in a body, etc.). The blank, rod, tube, etc. can be cut or otherwise formed by one or more processes (e.g., centerless grinding, turning, electropolishing, drawing process, grinding, laser cutting, shaving, polishing, EDM cutting, etching, micro-machining, laser micro-machining, laser micro-machining, micro-molding, machining, etc.). In one non limiting embodiment of the invention, the metal alloy blank, rod, tube, etc. is at least partially cut by a laser. The laser is typically desired to have a beam strength which can heat the metal alloy blank, rod, tube, etc. to a temperature of at least about 2200-2300° C. In one non-limiting aspect of this embodiment, a pulsed Nd:YAG neodymium-doped yttrium aluminum garnet (Nd:$Y_3Al_5O_{12}$) or $CO_2$ laser is used to at least partially cut a pattern of medical device out of the metal alloy blank, rod, tube, etc. In another and/or alternative non-limiting aspect of this embodiment, the cutting of the metal alloy blank, rod, tube, etc. by the laser can occur in a vacuum environment, an oxygen reducing environment, or an inert environment; however, this is not required. It has been found that laser cutting of the blank, rod, tube, etc. in a non-protected environment can result in impurities being introduced into the cut blank, rod, tube, etc., which introduced impurities can induce micro-cracking of the blank, rod, tube, etc. during the cutting of the blank, rod, tube, etc. One non-limiting oxygen reducing environment includes a combination of argon and hydrogen; however, a vacuum environment, an inert environment, or other or additional gasses can be used to form the oxygen reducing environment. In still another and/or alternative non-limiting aspect of this embodiment, the metal alloy blank, rod, tube, etc. is stabilized so as to limit or prevent vibration of the blank, rod, tube, etc. during the cutting process. The apparatus used to stabilize the blank, rod, tube, etc. can be formed of molybdenum, rhenium, tungsten, tantalum, cobalt, chromium, molybdenum TZM alloy, ceramic, etc. so as to not introduce contaminants to the blank, rod, tube, etc. during the cutting process; however, this is not required. Vibrations in the blank, rod, tube, etc. during the cutting of the blank, rod, tube, etc. can result in the formation of micro-cracks in the blank, rod, tube, etc. as the blank, rod, tube, etc. is cut. The average amplitude of vibration during the cutting of the blank, rod, tube, etc. is generally no more than about 150% the wall thickness of the blank, rod, tube, etc.; however, this is not required. In one non-limiting aspect of this embodiment, the average amplitude of vibration is no more than about 100% the wall thickness of the blank, rod, tube, etc. In another non-limiting aspect of this embodiment, the average amplitude of vibration is no more than about 75% the wall thickness of the blank, rod, tube, etc. In still another non-limiting aspect of this embodiment, the average amplitude of vibration is no more than about 50% the wall thickness of the blank, rod, tube, etc. In yet another non-limiting aspect of this embodiment, the average amplitude of vibration is no more than about 25% the wall thickness of the blank, rod, tube, etc. In still yet another non-limiting aspect of this embodiment, the average amplitude of vibration is no more than about 15% the wall thickness of the blank, rod, tube, etc.

In still yet another and/or alternative non-limiting aspect of the present invention, the metal alloy blank, rod, tube, etc., after being formed to the desired medical device, can be cleaned, polished, sterilized, nitrided, etc. for final processing of the medical device. In one non-limiting embodiment of the invention, the medical device is electro-polished. In one non-limiting aspect of this embodiment, the medical device is cleaned prior to being exposed to the polishing solution; however, this is not required. The cleaning process, when used, can be accomplished by a variety of techniques such as, but not limited to, 1) using a solvent (e.g., acetone, methyl alcohol, etc.) and wiping the medical device with a Kimwipe or other appropriate towel, and/or 2) by at least partially dipping or immersing the medical device in a solvent and then ultrasonically cleaning the medical device. As can be appreciated, the medical device can be cleaned in other or additional ways. In another and/or alternative non-limiting aspect of this embodiment, the polishing solution can include one or more acids. One non-limiting formulation of the polishing solution includes about 10-80 percent by volume sulfuric acid. As can be appreciated, other polishing solution compositions can be used. In still another and/or alternative non-limiting aspect of this embodiment, about 5-12 volts are directed to the medical device during the electro-polishing process; however, other voltage levels can be used. In yet another and/or alternative non-limiting aspect of this embodiment, the medical device is rinsed with water and/or a solvent and allowed to dry to remove polishing solution on the medical device.

The use of the novel alloy to form all or a portion of the medical device can result in several advantages over medical devices formed from other materials. These advantages include, but are not limited to:

The novel alloy has increased strength as compared with stainless steel or chromium-cobalt alloys, thus less quantity of novel alloy can be used in the medical device to achieve similar strengths as compared to medical devices formed of different metals. As such, the resulting medical device can be made smaller and less bulky by use of the novel alloy without sacrificing the strength and durability of the medical device. The medical device can also have a smaller profile, thus can be inserted into smaller areas, openings and/or passageways. The increased strength of the novel alloy also results in the increased radial strength of the medical device. For instance, the thickness of the walls of the medical device and/or the wires used to form the medical device can be made thinner and achieve a similar or improved radial strength as compared with thicker walled medical devices formed of stainless steel or cobalt and chromium alloy.

The novel alloy has improved stress-strain properties, bendability properties, elongation properties and/or flexibility properties of the medical device as compared with stainless steel or chromium-cobalt alloys, thus resulting in an increase life for the medical device. For instance, the medical device can be used in regions that subject the medical device to repeated bending. Due to the improved physical properties of the medical device from the novel alloy, the medical device has improved resistance to fracturing in such frequent bending environments. These improved physical properties at least in part result from the composition of the novel alloy; the grain size of the novel alloy; the carbon, oxygen and nitrogen content of the novel alloy; and/or the carbon/oxygen ratio of the novel alloy.

The novel alloy has a reduced degree of recoil during the crimping and/or expansion of the medical device as compared with stainless steel or chromium-cobalt alloys. The medical device formed of the novel alloy better maintains its crimped form and/or better maintains its expanded form after expansion due to the use of the novel alloy. As such, when the medical device is to be mounted onto a delivery device when the medical device is crimped, the medical device better maintains its smaller profile during the insertion of the medical device in a body passageway. Also, the medical device better maintains its expanded profile after expansion so as to facilitate in the success of the medical device in the treatment area.

The novel alloy has improved radiopaque properties as compared to standard materials such as stainless steel or cobalt-chromium alloy, thus reducing or eliminating the need for using marker materials on the medical device. For instance, the novel alloy is at least about 10-20% more radiopaque than stainless steel or cobalt-chromium alloy.

The novel alloy is less of an irritant to the body than stainless steel or cobalt-chromium alloy, thus can result in reduced inflammation, faster healing, increased success rates of the medical device. When the medical device is expanded in a body passageway, some minor damage to the interior of the passageway can occur. When the body begins to heal such minor damage, the body has less adverse reaction to the presence of the novel alloy than compared to other metals such as stainless steel or cobalt-chromium alloy.

One non-limiting object of the present invention is the provision of a medical device that is at least partially formed of a novel alloy.

Another and/or alternative non-limiting object of the present invention is the provision of a medical device having improved procedural success rates.

Still another and/or alternative non-limiting object of the present invention is the provision of a medical device that is formed of a material that improves the physical properties of the medical device.

Yet another and/or alternative non-limiting object of the present invention is the provision of a medical device that is at least partially formed of a novel alloy that has increased strength and can also be used as a marker material.

Still yet another and/or alternative non-limiting object of the present invention is the provision of a medical device that at least partially includes a novel alloy that enables the medical device to be formed with less material without sacrificing the strength of the medical device as compared to prior medical devices.

Still yet another and/or alternative non-limiting object of the present invention is the provision of a medical device that is simple and cost effective to manufacture.

A further and/or alternative non-limiting object of the present invention is the provision of a medical device that is at least partially coated with one or more polymer coatings.

Still a further and/or alternative non-limiting object of the present invention is the provision of a medical device that is coated with one or more biological agents.

Yet a further and/or alternative non-limiting object of the present invention is the provision of a medical device that has one or more polymer coatings to at least partially control the release rate of one or more biological agents.

Still yet a further and/or alternative non-limiting object of the present invention is the provision of a medical device that includes one or more surface structures and/or micro-structures.

Still a further and/or alternative non-limiting object of the present invention is the provision of a method and process for forming a novel alloy into a medical device.

Another and/or alternative non-limiting object of the present invention is the provision of a medical device that includes one or more surface structures, micro-structures and/or internal structures and a protective coating that at least partially covers and/or protects such structures.

Yet another and/or alternative non-limiting object of the present invention is the provision of a medical device that includes one or more markers.

Still another and/or alternative non-limiting object of the present invention is the provision of a medical device that includes and/or is used with one or more physical hindrances.

Still yet another and/or alternative non-limiting object of the present invention is the provision of a medical device that can be used in conjunction with one or more biological agents not on or in the medical device.

A further and/or alternative non-limiting object of the present invention is the provision of a method and process for forming a novel alloy that inhibits or prevent the formation of micro-cracks during the processing of the alloy into a medical device.

Still a further and/or alternative non-limiting object of the present invention is the provision of a medical device that includes CNT.

Another and/or alternative non-limiting object of the present invention is the provision of a method and process for forming a novel alloy that inhibits or prevents in the introduction of impurities into the alloy during the processing of the alloy into a medical device.

Still another and/or alternative non-limiting object of the present invention is the provision of a method and process for forming a novel alloy that has inhibits or prevents crack propagation and/or fatigue failure.

Yet another and/or alternative non-limiting object of the present invention is the provision of a medical device that is used in orthopedics (e.g., orthopedic device; nail; rod; screw; post; cage; plate; pedicle screw; cap; hinge; joint system; wire; anchor; spacer; shaft; spinal implant; anchor; disk; ball; tension band; locking connector; bone implant; prosthetic implant or device to repair, replace and/or support a bone; etc.), which medical device may or may not be expandable.

Yet another and/or alternative non-limiting object of the present invention is the provision of a medical device that is in the form of an implant for insertion into a body passageway (e.g., PFO device, stent, valve, spinal implant, vascular implant; graft, guide wire, sheath, stent catheter, electrophysiology catheter, hypotube, catheter, etc.), which medical device may or may not be expandable.

Still yet another and/or alternative non-limiting object of the present invention is the provision of a medical device that is used in dentistry and orthodontics (e.g., dental restorations, dental implants, crowns, bridges, braces, dentures, wire, anchors, spacers, retainers, tubes, pins, screws, posts, rods, plates, palatal expander, orthodontic headgear, orthodontic archwire, teeth aligners, quadhelix, etc.). One non-limiting medical device that is used in dentistry and orthodontics is in the form of a dental implant. The dental implant for insertion into bone generally includes an implant anchor having a connection arrangement (e.g., an interlocking thread, etc.). The dental implant can include a plurality of keys disposed about the distal end of the abutment, which distal end is capable of being affixed to the prosthetic tooth or dental appliance; an implantable anchor having a proximal and distal end, a plurality of female keyways defined into the proximal end of the anchor, the keyways capable of coupling to the male keys of the abutment and thereby preventing relative rotation of the abutment and anchor; however, this is not required. The dental implant can optionally include a repository bore perpendicular to the longitudinal bore defined in a distal portion of the anchor. The repository bore is cut through a portion of the anchor creating very sharp cutting edges to become self-tapping. The repository bore also can optionally serve as a repository for the bone chips created during the thread cutting process. One non-limiting dental implant is described in U.S. Pat. No. 7,198,488, which is incorporated herein by reference. The dental implant has a cylindrical anchoring head formed unitarily with a screw element. The screw element, usually made of the metal alloy of the present invention or titanium with a roughened surface, and is to be screwed into the recipient jaw bone. The anchoring head which can be formed of the metal alloy of the present invention is adapted to have a prosthetic tooth mounted on it.

A further and/or alternative non-limiting object of the present invention is the provision of a method and process for forming a novel metal alloy that inhibits or prevents in the introduction of impurities into the alloy during the processing of the alloy into a medical device.

These and other advantages will become apparent to those skilled in the art upon the reading and following of this description.

Other or additional features of the invention are disclosed in U.S. Pat. Nos. 7,488,444; 7,452,502; 7,540,994; 7,452,501; 8,398,916; U.S. Ser. No. 12/373,380; U.S. Ser. No. 61/816,357; U.S. Ser. No. 61/959,260; U.S. Ser. No. 61/871,902; U.S. Ser. No. 61/881,499; PCT/US2013/045543; and PCT/US2013/062804, which are all incorporated by reference herein.

Other or additional features of the invention are disclosed in U.S. Pat. Nos. 7,488,444; 7,452,502; 7,540,994; 7,452,501; 8,398,916; U.S. Ser. No. 12/373,380; U.S. Ser. No. 61/816,357; U.S. Ser. No. 61/959,260; U.S. Ser. No. 61/871,902; U.S. Ser. No. 61/881,499; PCT/US2013/045543; PCT/US2013/062804, and PCT/US2014/033262, which are all incorporated by reference herein.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
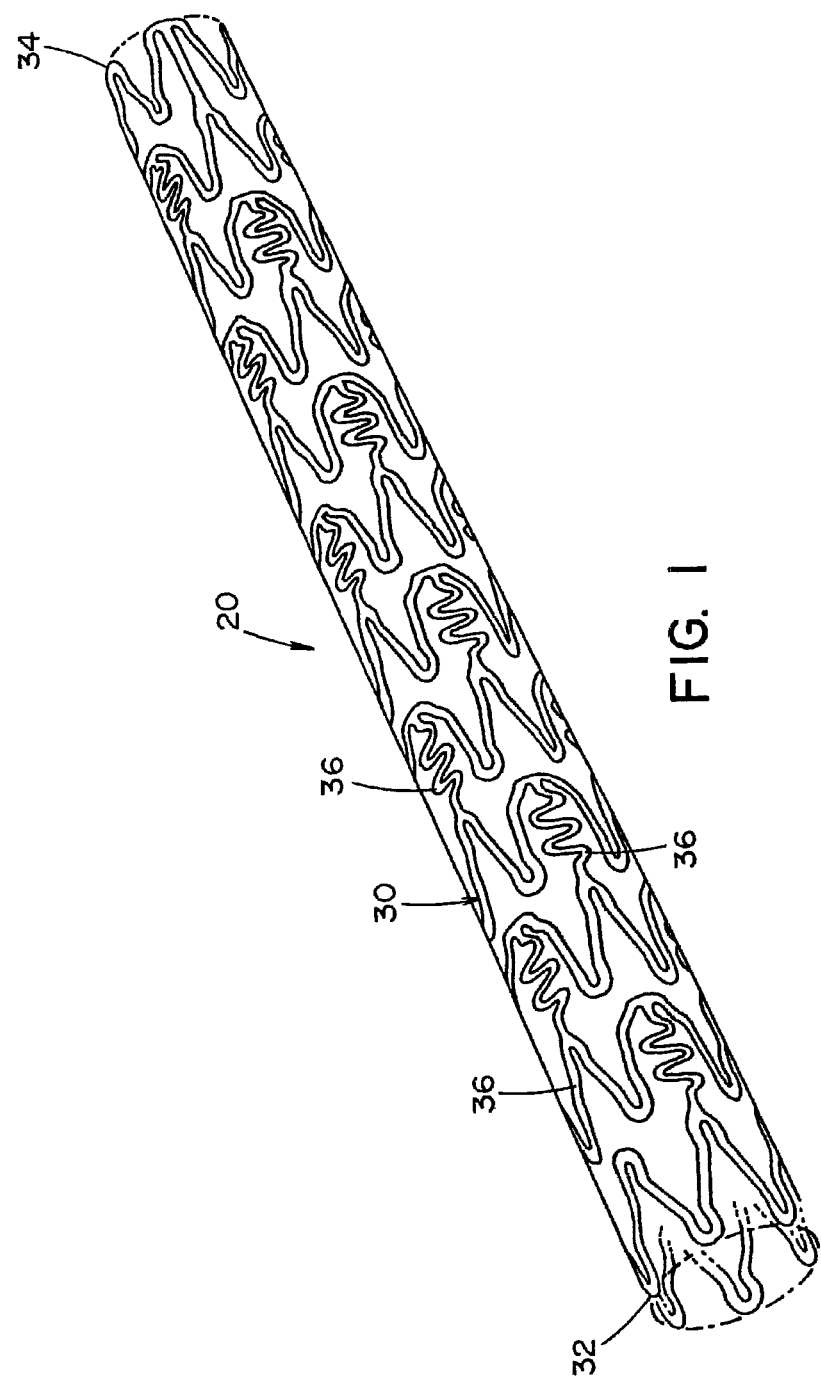
FIG. 1 is a perspective view of a section of a non-limiting medical device in the form of an unexpanded stent which permits delivery of the stent into a body passageway; and, FIG. 2 is one non-limiting process in accordance with the invention for manufacturing a medical device from a molybdenum and rhenium alloy, cobalt chromium, tungsten and tantalum alloy, or other type of metal alloy.

Referring now to the drawings wherein the showing is for the purpose of illustrating preferred embodiments of the invention only and not for the purpose of limiting the same, FIG. 1 discloses a medical device in the form of a stent for use in a body passageway. The stent is particularly useful in the cardiovascular field; however, the stent can be used in other medical fields such as, but not limited to, orthopedics, cardiology, pulmonology, urology, nephrology, gastrointerology, gynecology, otolaryngology or surgical fields. Additionally or alternatively, the medical device is not limited to a stent, thus can be in the form of many other medical devices (e.g., orthopedic implant, orthopedic device, PFO (patent foramen ovale) device, valve, spinal implant, vascular implant, graft, guide wire, sheath, stent catheter, electrophysiology catheter, hypotube, catheter, staple, cutting device, any type of implant, pacemaker, dental implant, bone implant, prosthetic implant or device to repair, replace and/or support a bone and/or cartilage, nail, rod, screw, post, cage, plate, pedicle screw, spinal rod, cap, hinge, joint system, wire, anchor, spacer, shaft, anchor, disk, ball, tension band, locking connector, or other structural assembly that is used in a body to support a structure, mount a structure and/or repair a structure in a body, dental restorations, crowns, bridges, braces, dentures, retainers, tubes, pins, palatal expander, orthodontic headgear, orthodontic archwire, teeth aligners, quadhelix, etc.).

The stent, when used for vascular applications, can be used to addresses various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophlebitis, thrombocytopenia or bleeding disorders.

As illustrated in FIG. 1, stent 20 is in the form of an expandable stent that includes at least one tubular shaped body member 30 having a first end 32, a second end 34, and member structures 36 disposed between the first and second ends. As can be appreciated, the stent can be formed of a plurality of body members connected together. Body member 30 has a first outer cross-sectional area or diameter which permits delivery of the body member into a body passageway. The first outer cross-sectional area or diameter of the body member is illustrated as substantially constant along the longitudinal length of the body member. As can be appreciated, the body member can have a varying first outer cross-sectional area or diameter along at least a portion of the longitudinal length of the body member. The body member also has a second expanded outer cross-sectional area or diameter, not shown. The second outer cross-sectional area or diameter typically can vary in size; however, the second outer cross-sectional area or diameter can be non-variable in size. The stent can be expanded in a variety of ways such as by a balloon. A balloon expandable stent is typically pre-mounted or crimped onto an angioplasty balloon catheter. A balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment area.

One or more surfaces of the stent can be treated so as to have generally smooth surfaces; however, this is not required. Generally, one or more ends of the stent are treated by filing, buffing, polishing, grinding, coating, and/or the like to remove or reduce the number of rough and/or sharp surfaces; however, this is not required. The smooth surfaces of the ends reduce potential damage to surrounding tissue as the stent is positioned in and/or expanded in a body passageway.

The stent can be at least partially coated with one or more therapeutic agents (not shown). One or more polymers (not shown) can be used in conjunction with the one or more therapeutic agents to 1) facilitate in the bonding of the one or more therapeutic agents to the stent, and/or 2) at least partially control the release of one or more therapeutic agents from the stent.

Figure 2:
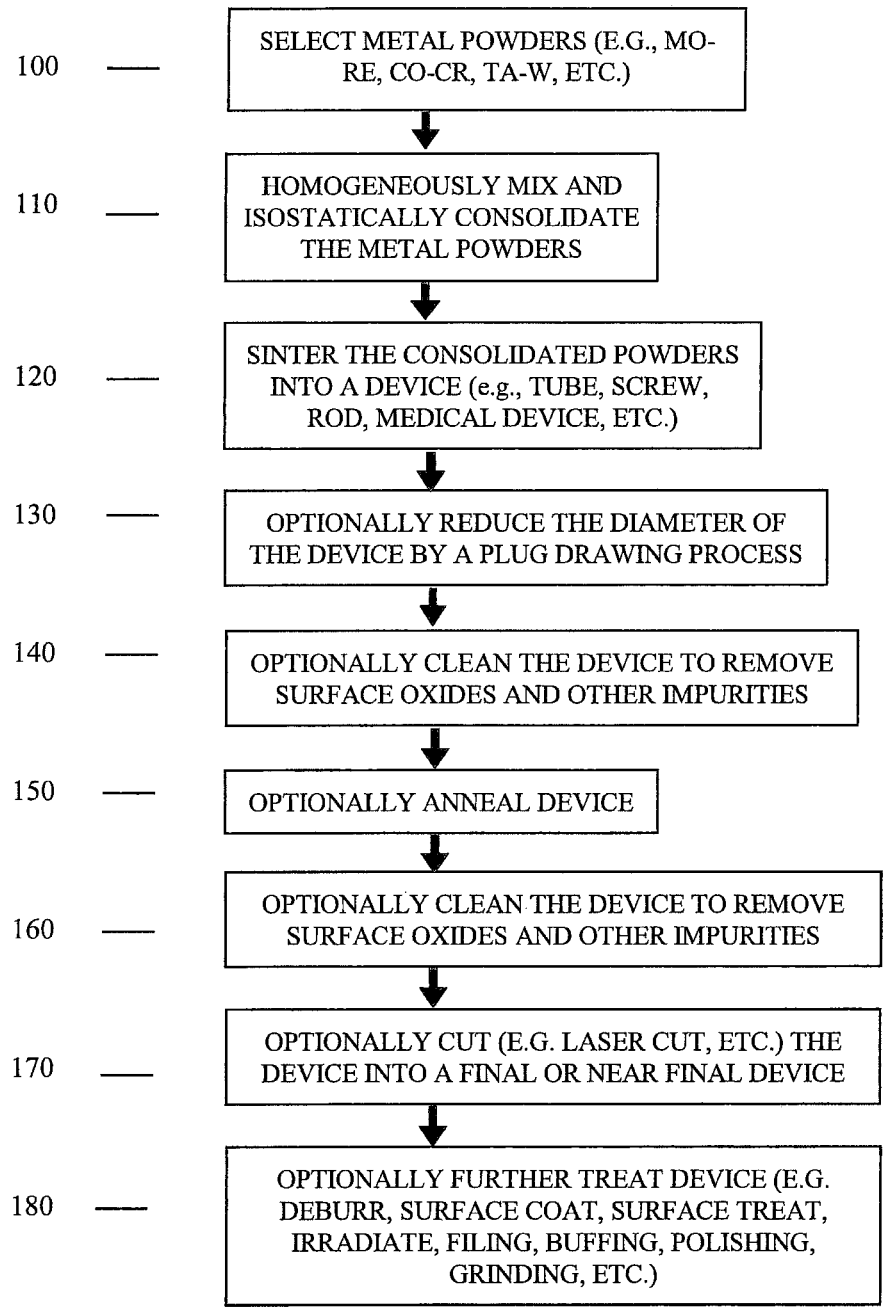

Referring now to FIG. 2, there is illustrated one non-limiting process for forming the stent as illustrated in FIG. 1 or some other type of medical device. The medical device can be formed of different types of metal alloys. The present invention is particularly directed to forming all or a portion of a medical device such as a stent from metal alloys that are difficult to work with such as alloys of molybdenum, titanium, yttrium, zirconium, rhenium, tantalum, cobalt, chromium and/or tungsten.

When the medical device is formed of 1) molybdenum and rhenium alloy, 2) molybdenum and rhenium alloy with small additions of other metals (e.g., titanium, yttrium, and/or zirconium), 3) tungsten and tantalum, 4) tungsten and tantalum and small additions of other metals, 5) cobalt and chromium, or some other metal alloy, medical device that is formed from such metal alloys can be form in a variety of ways in accordance with the present invention. Process step 100 illustrates that metal powders of the alloy are selected to form a tube, rod or some other structure of the medical device. The powders of metal alloys generally constitute a majority weight percent of the medical device; however, this is not required. The purity of the metal powders is selected to minimize the carbon, oxygen and nitrogen content in the metal powder; however, this is not required.

After the metal powders have been selected, the metal powders are substantially homogeneously mixed together as illustrated in process step 110. After the metal powders are mixed together, the metal powders are isostatically consolidated to form in a tube, rod or some other form for the medical device. In some situations, the metal powders can be formed into the final or near final form of the medical device (e.g., screw, etc.). One non-limiting isostatic consolidation process is a cold isostatic pressing (CIP) process. The isostatic consolidation process typically occurs in a vacuum environment (e.g., less than about $1\text{-}10^5$ Torr, etc.), an oxygen reducing environment, or in an inert atmosphere; however, this is not required. The average density of the metal tube obtained by the isostatic consolidation process is about 80-90% of the final average density of the final medical device that includes the metal alloy.

One non-limiting composition of the metal alloy is a solid solution of about 44-48 wt % rhenium and about 52-56 wt % molybdenum. One non-limiting metal alloy can include about 44.5-47.5 wt % Re and 52.5-55.5 wt % Mo, a weight percent of Re plus Mo of at least about 99.9%, and no more than about 0.2 weight impurities. Another non-limiting composition of the tube is a solid solution of about 44-48 wt % rhenium, about 52-56 wt % molybdenum, up to about 0.5 wt % Ti, Y and/or Zr, and no more than about 0.2 weight impurities. One non-limiting metal alloy can include a majority weight percent of Mo and Re and an additional metal selected from Ti, Y and/or Zr. One non-limiting metal alloy composition includes about 44-48 wt % Re, about 52-56 wt % Mo, and up to about 0.5 wt % Ti, Y and/or Zr. Another non-limiting metal alloy composition includes about 44.5-47.5 wt % Re, 52.5-55.5 wt % Mo, a weight percent of Mo plus Re plus Ti, Y and/or Zr that is at least about 99.9%, 0.3-0.4 wt % Ti, 0.06-0.1 wt % Zr, 0-0.05 wt % Y, a weight ratio of Ti:Zr of 1-3:1, and no more than about 0.2 weight impurities.

After the metal powder has been selected and pressed together, the metal powder is sintered to fuse the metal powders together and to form the tube, rod or some other form for the medical device. The sinter of the metal powders occurs at an appropriate temperature for the particular metal alloy. For a Mo—Re alloy, a sintering temperature of about 2000-2500° C. for about 5-120 minutes can be used; however, other temperatures and/or sintering time can be used. The sintering of the metal powder typically takes place in an oxygen reducing environment to inhibit or prevent impurities from becoming embedded in the metal alloy and/or to further reduce the amount of carbon and/or oxygen in the metal alloy; however, this is not required. After the sintering process, the solid solution of the metal alloy generally has an as-sintered average density of about 90-99% the minimum theoretical density of the metal alloy. Typically, for a Mo—Re sintered metal alloy, the final average density is about 13-14 gm/cc. Higher sintering temperatures will generally be required (e.g., 2000-3000° C.) and greater average densities will be obtained (e.g., greater than 14 gm/cc) when forming tungsten and tantalum alloys. For other types of alloys, the sinter temperature and time and the final average density of the metal alloy may be different.

When the metal powders are formed into a rod or tube, the length of the formed rod or tube is typically about 48 inches or less; however, longer lengths can be formed. Generally, when the final medical device is to be a stent or a rod, a tube is first formed. For other types of medical devices, a tube may not be formed. In one non-limiting arrangement, the length of the rod or tube is about 8-20 inches. The average concentricity deviation of the rod or tube is typically about 1-18% for use in forming a stent. In one non-limiting tube configuration, the tube has an inner diameter of about 0.31 inch (i.e., 0.0755 sq. in. cross-sectional area) plus or minus about 0.002 inch and an outer diameter of about 0.5 inch (i.e., 0.1963 sq. in. cross-sectional area) plus or minus about 0.002 inch. The wall thickness of the tube is about 0.095 inch plus or minus about 0.002 inch. As can be appreciated, this is just one example of many different sized tubes that can be formed.

In another alternative tube forming process, a rod of metal alloy is first formed from one or more ingots of metal alloy. These ingots can be formed by an arc melting process; however, other or additional process can be used to form the metal ingots. The ingots can be formed into a rod by extruding the ingots through a die to form a rod of a desired outer cross-sectional area or diameter. The length of the formed rod is typically about 48 inches or less; however, longer lengths can be formed. In one non-limiting arrangement, the length of the rod or tube is about 8-20 inches. After the rod is formed, the rod is hollowed by EDM to form a tube. The inner cross-sectional area or diameter of the hollowed tube is carved to the exact inner cross-sectional area or diameter by a wire EDM process. As can be appreciated, the rod can be drawn down to an intermediate size, and then hollowed by EDM to a tube, and then further drawn down to a desired size. In one non-limiting tube configuration, the tube has an inner diameter of about 0.2-0.4 inch plus or minus about 0.005 inch and an outer diameter of about 0.4-0.6 inch plus or minus about 0.005 inch. The wall thickness of the tube is about 0.001-0.15 inch, and generally about 0.001-0.1 inch, and typically about 0.04-0.1 inch plus or minus about 0.005 inch. As can be appreciated, this is just one example of many different sized tubes that can be formed.

After the tube is formed, the tube can be drawn down to a desired OD and/or wall thickness. When the tube is drawn down, the annealing temperature and time is generally adjusted based on the wall thickness of the tube. For example, the annealing temperature for a molybdenum and rhenium alloy should be about 1500° C. for 30 minutes for drawn tubes with wall thickness from 0.050-0.015", 1475° C. for 30 minutes for drawn tubes with wall thickness from 0.015-0.080", and about 1425° C. for 30 minutes for drawn tubes with wall thickness from 0.005-0.002". Slight differences in temperature and/or annealing times may be used for tungsten and tantalum alloys or other types of metal alloys. The annealing temperature is generally reduced for thinner walls in order to obtain a smaller grain structure for the tubing. For Mo—Re alloys, the annealing process can optionally take place in a hydrogen atmosphere or in a vacuum. For Mo—Re alloys, after each annealing process, the grain size of the tubing should be no greater than about an ASTM grain number 6, and typically no greater than an ASTM grain number of 8. A final grain size of the tube of Mo—Re alloy can be up to an ASTM grain number of 14. For other metal alloys, the grain size can be different. The grain size in the final tube should be generally uniform. For a Mo—Re alloy, the final tube generally has a minimum amount of sigma phase, which sigma phase has a generally spherical, elliptical or tetragonal shape. When the tubing is formed primarily of molybdenum and rhenium, the sigma phase is generally made up of both rhenium and molybdenum, with a heavier concentration of rhenium. When a shape other than a rod or tube is formed, the formed metal allot can also be subjected to one or more annealing steps to achieve the desired properties of the metal alloy.

The formed tube, rod or other metal alloy structure can be cleaned and/or polished after being formed; however, this is not required. The cleaning and/or polishing of the tube, rod or other metal alloy structure is used to remove impurities and/or contaminants from the surfaces of the tube, rod or other metal alloy structure and/or to remove rough areas from the surface of the tube, rod or other metal alloy structure. Impurities and contaminants (e.g., carbon, oxygen, lubricants, etc.) can become incorporated into the metal alloy during the processing of the tube, rod or other metal alloy structure. The inclusion of impurities and contaminants in the metal alloy can result in premature microcracking of the metal alloy and/or the adverse effect on one or more physical properties of the metal alloy. The cleaning of the tube, rod or other metal alloy structure can be accomplished by a variety of techniques such as, but not limited to, 1) using a solvent (e.g., acetone, methyl alcohol, etc.) and wiping the metal alloy with a Kimwipe or other appropriate towel, and/or 2) by at least partially dipping or immersing the metal alloy in a solvent and then ultrasonically cleaning the metal alloy. As can be appreciated, the tube, rod or other metal alloy structure can be cleaned in other or additional ways. The tube, rod or other metal alloy structure, when polished, is generally polished by use of a polishing solution that typically includes an acid solution; however, this is not required. In one non-limiting example, the polishing solution includes sulfuric acid; however, other or additional acids can be used. In one non-limiting polishing solution, the polishing solution can include by volume 60-95% sulfuric acid and 5-40% de-ionized water (DI water). The polishing solution can be increased in temperature during the making of the solution and/or during the polishing procedure. One non-limiting polishing technique that can be used is an electro-polishing technique. The time used to polish the metal alloy is dependent on both the size of the tube, rod or other metal alloy structure and the amount of material that needs to be removed from the tube, rod or other metal alloy structure. The tube, rod or other metal alloy structure can be processed by use of a two-step polishing process wherein the metal alloy piece is at least partially immersed in the polishing solution for a given period (e.g., 0.1-15 minutes, etc.), rinsed (e.g., DI water, etc.) for a short period of time (e.g., 0.02-1 minute, etc.), and then flipped over and at least partially immersed in the solution again for the same or similar duration as the first time; however, this is not required. The tube, rod or other metal alloy structure can be rinsed (e.g., DI water, etc.) for a period of time (e.g., 0.01-5 minutes, etc.) before rinsing with a solvent (e.g., acetone, methyl alcohol, etc.); however, this is not required. The tube, rod or other metal alloy structure can be dried (e.g., exposure to the atmosphere, maintained in an inert gas environment, etc.) on a clean surface. These polishing procedures can be repeated until the desired amount of polishing of the tube, rod or other metal alloy structure is achieved. Typically, after the tube, rod or other metal alloy structure has been first formed and/or hollowed out, the inner surface (i.e., the inner passageway of the tube) and the outer surface of the tube, rod or other metal alloy structure are polished. The polishing techniques for the inner and outer surfaces of the tube, rod or other metal alloy structure can be the same or different. The inner surface and/or outer surface of the tube, rod or other metal alloy structure is also typically polished at least after one drawing process. As can be appreciated, the inner and/or outer surface of the tube, rod or other metal alloy structure can be polished after each drawing process, and/or prior to each annealing process. A slurry honing polishing process can be used to polishing the inner and/or outer surface of the tube, rod or other metal alloy structure; however, other or additional processes can be used.

After the tube has been formed (e.g., sintering process, extrusion process, etc.), and optionally cleaned, the tube is then drawn through a die one or more times to reduce the inner and outer cross-sectional area or diameter of the tube and the wall thickness of the tube to the desired size. As illustrated in process step 130, the tube can be optionally reduced in size by the use of a drawing process such as, but not limited to, a plug drawing process. During the drawing process, the tube is heated. During the drawing process, the tube can be protected in a reduced oxygen environment such as, but not limited to, an oxygen reducing environment or inert environment. One non-limiting oxygen reducing environment includes argon and about 1-10 volume percent hydrogen. When the temperature of the drawing process is less than about 400-450° C., the need to protect the tube from oxygen is significantly diminished. As such, a drawing process that occurs at a temperature below about 400-450° C. can optionally occur in air. At higher temperatures, the tube is generally drawn in an oxygen reducing environment or an environment. Typically, the drawing temperature for a Mo—Re alloy does not exceed about 500-550° C. A mandrel removal process can be used during the drawing process for the tube to improve the shape and/or uniformity of the drawn tube; however, this is not required. The amount of outer cross-sectional area or diameter draw down of the tube each time the tube is plug drawn is typically no more than about 10-20%. Controlling the degree of draw down facilitates in preventing the formation of micro-cracks during the drawing process. After each drawing process, the tube can be cleaned; however, this is not required. During the drawing process, the inner surface of the tube can be at least partially filled with a close-fitting rod. When a close-fitting rod is used, the metal rod is inserted into the tube prior to the tube being drawn through a die. The close-fitting rod is generally facilitates in maintaining a uniform shape and size of the tube during a drawing process. The close-fitting rod is generally an unalloyed metal rod; however, this is not required. Non-limiting examples of metals that can be used to form the close-fitting rod are tantalum and niobium. When a close-fitting rod is used, the close-fitting rod can be used for each drawing process or for selected drawing processes. Prior to the high temperature annealing of the tube, the close-fitting rod, when used, it removed from the tube. The tube can be heated to facilitate in the removal of the close-fitting rod from the tube; however, this is not required. When the tube is heated to remove the close-fitting rod, a Mo—Re alloy tube is generally not heated above about 1000° C., and typically about 600-800° C.; however, other temperatures can be used. When the tube is heated above about 400-450° C., a vacuum, an oxygen reducing environment or an inert environment is generally used to shield the tube from the atmosphere. As can also be appreciated, a close-fitting tube can also or alternatively be used during the formation of the tube during an extrusion process. Generally, after the close-fitting rod is removed from the tube, the inner and/or outer surface of the tube is polished; however, this is not required.

The tube is typically exposed to a nitriding step prior to drawing down the tube; however, this is not required. The layer of nitride compound that forms on the surface of the tube after a nitriding process has been found to function as a lubricating layer for the tube as the tube is drawn down to a smaller cross-sectional area or diameter. The nitriding process occurs in a nitrogen containing atmosphere at temperatures exceeding 400° C. Typically the nitriding process is about 5-15 minutes at a temperature of about 450-600° C. The nitrogen atmosphere can be an essentially pure nitrogen atmosphere, a nitrogen-hydrogen mixture, etc.

Prior to the tube being drawn down more than about 35-45% from its original outer cross-sectional area or diameter after the sintering process, the tube is optionally annealed as illustrated in process step 150. If the tube is to be further drawn down after being initially annealed, a subsequent annealing process generally is completed prior to the outer cross-sectional area or diameter of the tube being drawn down more than about 35-45% since a previous annealing process. As such, the tube generally is annealed at least once prior to the tube outer cross-sectional area or diameter being drawn down more than about 35-45% since being originally sintered or being previously annealed. This controlled annealing facilitates in preventing the formation of micro-cracks during the drawing process. The annealing process of for a Mo—Re tube typically takes place in a vacuum environment, an inert atmosphere, or an oxygen reducing environment (e.g., hydrogen, argon, argon and 1-10% hydrogen, etc.) at a temperature of about 1400-1600 C for a period of about 5-60 minutes; however, other temperatures and/or times can be used. The use of an oxygen reducing environment during the annealing process can be used to reduce the amount of oxygen in the tube. The chamber in which the tube is annealed should be substantially free of impurities such as, but not limited to, carbon, oxygen, and/or nitrogen. The annealing chamber typically is formed of a material that will not impart impurities to the tube as the tube is being annealed. One non-limiting material that can be used to form the annealing chamber is a molybdenum TZM alloy. The parameters for annealing the tube as the cross-sectional area or diameter and thickness of the tube is changed during the drawing process can remain constant or be varied. It has been found that good grain size characteristics of the tube can be achieved when the annealing parameters are varied during the drawing process. In one non-limiting processing arrangement, the annealing temperature of a Mo—Re tube having a wall thickness of about 0.015-0.05 inch is generally about 1480-1520° C. for a time period of about 5-40 minutes. In another non-limiting processing arrangement, the annealing temperature of a Mo—Re tube having a wall thickness of about 0.008-0.015 inch is generally about 1450-1480° C. for a time period of about 5-60 minutes. In another non-limiting processing arrangement, the annealing temperature of a Mo—Re tube having a wall thickness of about 0.002-0.008 inch is generally about 1400-1450° C. for a time period of about 15-75 minutes. As such, as the wall thickness is reduced, the annealing temperature is correspondingly reduced; however, the times for annealing can be increased. As can be appreciated, the annealing temperatures of the tube can be decreased as the wall thickness decreases, but the annealing times can remain the same or also be reduced as the wall thickness reduces. After each annealing process, the grain size of the metal in the tube should be no greater than 4 ASTM, typically no greater than 6 ASTM, more typically no greater than 7 ASTM, and even more typically no greater than about 7.5 ASTM. Grain sizes of 7-14 ASTM can be achieved by the annealing process of the present invention. It is believed that as the annealing temperature is reduced as the wall thickness reduces, small grain sizes can be obtained. The grain size of the metal in the tube should be as uniform as possible. In addition, the sigma phase of the metal in the tube should be as reduced as much as possible. The sigma phase is a spherical, elliptical or tetragonal crystalline shape in a Mo—Re metal alloy. The sigma phase is commonly formed of both rhenium and molybdenum, typically with a larger concentration of rhenium. After the final drawing of the tube, a final annealing of the tube can be done for final strengthening of the tube; however, this is not required. This final annealing process for a Mo—Re alloy, when used, generally occurs at a temperature of about 1425-1500° C. for about 20-40 minutes; however, other temperatures and/or time periods can be used. The grain structure can be altered using the final anneal process.

After each annealing process, the tube, rod or other structure can optionally be cooled at a fairly quick rate so as to inhibit or prevent sigma phase formations in the metal alloy; however, this is not required. Typically, a Mo—Re alloy tube is cooled at a rate of about 100-400° C. per minute, and more typically about 200-300° C. per minute. The tube is can be cooled in a variety of ways (e.g., subjecting the annealed tube to a cooling gas and/or cooling liquid, placing the annealed tube in a refrigerated environment, etc.).

Prior to each annealing process, the tube, rod or other structure is optionally cleaned and/or pickled to remove oxides and/or other impurities from the surface of the tube as illustrated in process step 140. Typically, the tube, rod or other structure is cleaned by first using a solvent (e.g., acetone, methyl alcohol, etc.) and wiping the metal alloy with a Kimwipe or other appropriate towel, and/or by at least partially dipping or immersing the tube in a solvent and then ultrasonically cleaning the metal alloy. As can be appreciated, the tube, rod or other structure can be cleaned other and/or additional ways. After the tube, rod or other structure has been cleaned by use of a solvent, the tube, rod or other structure is optionally further cleaned by use of a pickling process. The pickling process includes the use of one or more acids to remove impurities from the surface of the tube, rod or other structure. Non-limiting examples of acids that can be used as the pickling solution include, but are not limited to, nitric acid, acetic acid, sulfuric acid, hydrochloric acid, and/or hydrofluoric acid. The acid solution and acid concentration and time of pickling are selected to remove oxides and other impurities on the tube surface without damaging or over etching the surface of the tube, rod or other structure. During the pickling process, the tube, rod or other structure is fully or partially immersed in the pickling solution for a sufficient amount of time to remove the impurities from the surface of the tube, rod or other structure. After the tube, rod or other structure has been pickled, the tube, rod or other structure is typically rinsed with a solvent (e.g., acetone, methyl alcohol, etc.) to remove any pickling solution from the tube, rod or other structure and then the tube, rod or other structure is allowed to dry. The cleaning of the tube, rod or other structure prior to the tube being annealed removes impurities and/or other materials from the surfaces of the tube, rod or other structure that could become permanently embedded into the tube, rod or other structure during the annealing processes. These imbedded impurities could adversely affect the physical properties of the metal alloy as the tube, rod or other structure is formed into a medical device, and/or can adversely affect the operation and/or life of the medical device. As can be appreciated, the tube, rod or other structure can be again clean and/or pickled after being annealed and prior to be drawn down in the plug drawing process; however, this is not required.

Process steps 130-150 can be repeated as necessary until the rod or tube is drawn down to the desired size. In one non-limiting process, a tube that is originally formed after being sintered has an inner diameter of about 0.31 inch plus or minus about 0.002 inch, an outer diameter of about 0.5 inch plus or minus about 0.002 inch, and a wall thickness of about 0.095 inch plus or minus about 0.002 inch. After the tube has been fully drawn down, the tube has an outer diameter of about 0.070 inch, a wall thickness of about 0.0021-0.00362 inch, and the average concentricity deviation of less than about 10%. Such small sizes for stents which can be successfully used in a vascular system have heretofore not been possible when formed by other types of metal alloys. Typically, the wall thickness of stent had to be at least about 0.0027-0.003 inch, or the stent would not have sufficient radial force to maintain the stent in an expanded state after being expanded. The metal alloy of the present invention is believed to be able to have a wall thickness of as small as about 0.0015 inch and still have sufficient radial force to maintain a stent in an expanded state after being expanded. As such, when a tube is formed into a stent, the wall thickness of the tube can be drawn down to less than about 0.0027 inch to form a stent. As can be appreciated, this is just one example of many different sized tubes that can be formed by the process of the present invention.

Once the rod or tube has been drawn down to its final size, the rod or tube is typically cleaned (Process Step 140), annealed (Process Step 150) and then again cleaned (Process Step 160). The cleaning step of process step 160 can include merely solvent cleaning, or can also include pickling.

After the tube, rod or other structure has been cleaned in process step 160, the tube, rod or other structure can be optionally cut into the form of the desired medical device (e.g., a stent as illustrated in FIG. 1). The cutting of the tube, rod or other structure can be accomplished by use of a laser; however, this is not required. When a laser is used, the laser that is used to cut the tube, rod or other structure is selected so that it has a desired beam strength. When cutting Mo—Re alloys, the desired beam strength of the laser should be sufficient to obtain a cutting temperature of at least about 2350° C. Non-limiting examples of lasers that can be used include a pulsed Nd:YAG neodymium-doped yttrium aluminum garnet (Nd:$Y_3Al_5O_{12}$) or $CO_2$ laser. The cutting of tube, rod or other structure by the laser can occurs in an oxygen reducing environment such as an argon and 1-10 percent by volume hydrogen environment; however, a vacuum environment, an inert environment, or another type of oxygen reducing environment can be used. During the cutting of tube, rod or other structure, tube, rod or other structure is typically stabilized so as to inhibit or prevent vibration of tube, rod or other structure during the cutting process, which vibrations can result in the formation of micro-cracks in the tube as tube, rod or other structure. The tube, rod or other structure can be stabilized by an apparatus that will not introduce contaminates to the tube, rod or other structure during the cutting process; however, this is not required. The average amplitude of vibration during the cutting of the tube, rod or other structure is typically no more than about 50% the wall thickness of the tube, rod or other structure. As such, for a tube having a wall thickness of about 0.0024 inch, the average amplitude of vibration of the tube during the cutting process is no more than about 0.0012 inch.

After the medical device has been cut, the medical device can be further processed; however, this is not required. The one or more processes can include, but are not limited to, 1) electro-polishing the medical device, 2) treating one or more surfaces of the medical device to create generally smooth surfaces and/or other types of surfaces (e.g., filing, buffing, polishing, grinding, coating, nitriding, etc.), 3) at least partially coating the medical device with one or more therapeutic agents, 4) at least partially coating the medical device with one or more polymers, 5) forming one or more surface structures and/or micro-structures on one or more portions of the medical device, 6) inserting one or more markers on one or more portions of the medical device, and/or 7) straightening process for the medical device.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A method for forming a medical device comprising the steps of:

selecting a metal alloy, said metal alloy including greater than 50 weight percent molybdenum or a cobalt-chromium alloy, said metal alloy having an average density of up to about 14 gm/cc, said metal alloy is a molybdenum alloy that includes up to 99.9 wt. % molybdenum, said metal alloy is selected from the group consisting of MoHfC, $MoY_2O_3$, $MoCe_2O$, $MoY_2O_3Ce_2O$, MoW, $MoZrO_2$, and $MoLa_2O_3$; a) a weight percent of said hafnium in said MoHfC is about 0.8-1.4 weight percent and a weight percent of said carbon in said MoHfC is about 0.05-0.15, and said MoHfC has an elongation of greater than 10%, a UTS of 60-320 ksi, and a modulus of elasticity of >300 GPa; b) a weight percent of $La_2O_3$ in said $MoLa_2O_3$ is about 0.3-0.7, and a carbon content in said $MoLa_2O_3$ is no more than 150 ppm, and said $MoLa_2O_3$ has an elongation of greater than 10%, a UTS of 60-320 ksi, and a modulus of elasticity of >300 GPa; c) a weight percent of $Ce_2O$ in said $MoY_2O_3Ce_2O$ is about 0.04-0.1, a carbon content in said $MoY_2O_3Ce_2O$ is no more than 150 ppm, and a weight percent of $Y_2O_3$ in said $MoY_2O_3Ce_2O$ is about 0.3-0.5 weight percent, and said $MoY_2O_3Ce_2O$ has an elongation of greater than 10%, a UTS of 60-320 ksi, and a modulus of elasticity of >300 GPa; d) a weight percent of tungsten in said MoW is about 20-50 weight percent, a carbon content in said MoW is no more than 150 ppm, and said MoW has an elongation of greater than 10%, a UTS of 60-320 ksi, and a modulus of elasticity of >300 GPa; e) a weight percent of $ZrO_2$ in said $MoZrO_2$ is about 1.2-1.8, a carbon content in said $MoZrO_2$ is no more than 150 ppm, and said $MoZrO_2$ has an elongation of greater than 10%, a UTS of 60-320 ksi, and a modulus of elasticity of >300 Gpa;

forming said metal alloy into at least a portion of said medical device, said medical device in the form of an orthopedic device or an orthodontic device, said orthopedic device is selected from the group consisting of a orthopedic nail, orthopedic rod, orthopedic post, orthopedic cage, bone plate, pedicle screw, joint system, bone anchor, bone spacer, spinal implant, spinal disk, spinal ball, tension band, bone implant, and prosthetic implant; said orthodontic device is selected from the group consisting of a dental restoration, dental implant, crown, dental bridge, braces, dentures, tooth spacer, teeth retainer, dental plates, palatal expander, orthodontic headgear, orthodontic archwire, teeth aligners, and quadhelix; and, final finishing said medical device, said step of final finishing including one or more processes selected from the group consisting of annealing, pilgering, electro-plating, electro-polishing, chemical polishing, cleaning, pickling, nitriding, ion beam deposition or implantation, sputter coating, and vacuum deposition.

2. The method as defined in claim 1, wherein said metal alloy is formed into an intermediary shape in the form of a rod or tube prior to forming said medical device, said method further includes the steps of:
   i) drawing down said outer cross-sectional area of said rod or tube by a reducing mechanism;
   ii) annealing said rod or tube at an annealing temperature in an oxygen reducing environment or inert environment after said rod or tube has been drawn down;
   iii) cooling said annealed rod or tube at a rate of at least about 100° C. per minute;
   iv) drawing down said cross-sectional area of said rod or tube by the reducing mechanism after said rod or tube has been annealed; and,
   v) annealing said rod or tube at least one additional time at an annealing temperature that is lower temperature than at least one annealing temperature of a previous annealing of said rod or tube.

3. The method as defined in claim 2, including the step of nitriding said metal alloy to form a nitride layer on said metal alloy prior to at least one drawing down step, said step of nitriding including a) exposing at least a portion of said metal alloy to a nitriding gas that includes nitrogen, nitrogen and hydrogen, or combinations thereof, and b) exposing at least a portion of said metal alloy to a nitriding gas at a temperature of less than about 400° C. for at least about 1 minute.

4. The method as defined in claim 3, including the step of removing said nitride layer on said metal alloy prior to annealing said metal alloy.

5. The method as defined in claim 4, including the step of isostatically pressing metal powder together and subsequently sintering said metal powder in a controlled atmosphere to form said metal alloy, said metal alloy having an average density of about 0.7-0.95 a theoretical density of said metal alloy.

6. The method as defined in claim 5, wherein said metal alloy is MoHfC.

7. The method as defined in claim 5, wherein said metal alloy is $MoLa_2O_3$.

8. The method as defined in claim 5, wherein said metal alloy is $MoY_2O_3Ce_2O$.

9. The method as defined in claim 5, wherein said metal alloy is MoW.

10. The method as defined in claim 5, wherein said metal alloy is $MoZrO_2$.

11. The method as defined in claim 1, including the step of nitriding said metal alloy to form a nitride layer on said metal alloy prior to at least one drawing down step, said step of nitriding including a) exposing at least a portion of said metal alloy to a nitriding gas that includes nitrogen, nitrogen and hydrogen, or combinations thereof, and b) exposing at least a portion of said metal alloy to a nitriding gas at a temperature of less than about 400° C. for at least about 1 minute.

12. The method as defined in claim 1, including the step of isostatically pressing metal powder together and subsequently sintering said metal powder in a controlled atmosphere to form said metal alloy, said metal alloy having an average density of about 0.7-0.95 a theoretical density of said metal alloy.

13. The method as defined in claim 7, wherein said metal alloy is $MoCe_2O$.

14. The method as defined in claim 7, wherein said metal alloy is $MoY_2O_3$.

* * * * *